US011698527B2

(12) United States Patent
Chung et al.

(10) Patent No.: US 11,698,527 B2
(45) Date of Patent: Jul. 11, 2023

(54) CAPACITANCE-BASED EYE TRACKER

(71) Applicant: University of Washington, Seattle, WA (US)

(72) Inventors: Jae-Hyun Chung, Seattle, WA (US); Vigneshwar Sakthivelpathi, Seattle, WA (US); Sang-gyeun Ahn, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 17/727,644

(22) Filed: Apr. 22, 2022

(65) Prior Publication Data

US 2022/0350137 A1 Nov. 3, 2022

Related U.S. Application Data

(60) Provisional application No. 63/179,045, filed on Apr. 23, 2021.

(51) Int. Cl.
*G02B 27/01* (2006.01)
*A61B 3/10* (2006.01)
*A61B 3/113* (2006.01)
*G02B 27/00* (2006.01)

(52) U.S. Cl.
CPC ..... *G02B 27/0093* (2013.01); *G02B 27/0101* (2013.01); *A61B 3/113* (2013.01); *G02B 2027/0132* (2013.01); *G02B 2027/0187* (2013.01)

(58) Field of Classification Search
CPC ......... A61B 3/02; A61B 3/102; A61B 3/1025; A61B 3/113; A61B 3/1015; A61B 3/1225; A61B 3/024; G02B 27/00; G02B 27/01; G02C 11/10; G02C 7/04

USPC ......... 359/629–630; 351/200, 205, 206, 209, 351/210, 221–223, 246
See application file for complete search history.

(56) References Cited

U.S. PATENT DOCUMENTS

| 9,888,843 | B2 | 2/2018 | Moller | |
| 2016/0182899 | A1* | 6/2016 | Liu | H04N 13/31 |
| | | | | 348/54 |
| 2016/0353988 | A1* | 12/2016 | Moller | A61B 3/113 |
| 2017/0112433 | A1* | 4/2017 | Pugh | A61B 5/6821 |
| 2017/0344107 | A1* | 11/2017 | Aghara | G06F 3/011 |

(Continued)

FOREIGN PATENT DOCUMENTS

| CN | 107645921 A | * | 1/2018 | A61B 3/005 |
| KR | 20170133772 A | * | 12/2017 | G02F 1/15 |
| WO | WO9113584 A1 | * | 9/1999 | A61B 5/4362 |

OTHER PUBLICATIONS

International Search Report and Written Opinion dated Aug. 9, 2022, issued in International Application No. PCT/US2022/026022, filed Apr. 22, 2022, 8 pages.

(Continued)

*Primary Examiner* — Dawayne Pinkney
(74) *Attorney, Agent, or Firm* — Christenson O'Connor Johnson Kindness PLLC

(57) ABSTRACT

An eye-tracking system, including at least one vertical capacitance sensor, configured to measure the vertical position of a cornea of a user's eye by sensing a position of an eyelid of the user; and at least one horizontal capacitance sensor, configured to measure the horizontal position of the cornea of the user's eye by sensing a position of the user's eyeball.

29 Claims, 20 Drawing Sheets

(56) References Cited

U.S. PATENT DOCUMENTS

| | | |
|---|---|---|
| 2018/0125358 A1 | 5/2018 | Moller |
| 2018/0173011 A1 | 6/2018 | Barrows |
| 2020/0196949 A1 | 6/2020 | Lee |

OTHER PUBLICATIONS

Sakthivelpathi, Vigneshwar, et al. "Capacitive eye tracker made of fractured carbon nanotube-paper composites for wearable applications." Sensors and Actuators A: Physical 344 (2022): 113739.

Acuna O, V., Aqueveque, P., Pino, E.J., 2014. Eye-tracking capabilities of low-cost EOG system. Annual International Conference of the IEEE Engineering in Medicine and Biology Society. IEEE Engineering in Medicine and Biology Society. Annual International Conference 2014, 610-613.

Alexander, Robert G., Stephen L. Macknik, and Susana Martinez-Conde. "Microsaccade characteristics in neurological and ophthalmic disease." Frontiers in Neurology 9 (2018): 144.

Anantram, M. P., Mark S. Lundstrom, and Dmitri E. Nikonov "Modeling of nanoscale devices" arXiv:cond-mat/0610247v2 [cond-mat.mes-hall] Feb. 20, 2007.

Anantram MP, Leonard F. Physics of carbon nanotube electronic devices. Reports on Progress in Physics. 2006;69 (3):507-61. doi: 10.1088/0034-4885/69/3/r01. PubMed PMID: WOS:000236697700001.

Anantram, M. P., and T. R. Govindan. "Transmission through carbon nanotubes with polyhedral caps." Physical Review B 61.7 (2000): 5020.

Avanzini, Giuliano, et al. "Oculomotor disorders in Huntington's chorea." Journal of Neurology, Neurosurgery & Psychiatry 42.7 (1979): 581-589.

Fuchs AF, Kaneko CR, Scudder CA. Brainstem control of saccadic eye movements. Annual review of neuroscience. 1985;8:307-37. Epub Jan. 1, 1985. doi: 10.1146/annurev.ne.08.030185.001515. PubMed PMID: 3920944.

Keller EL, Gandhi NJ, Shieh JM. Endpoint accuracy in saccades interrupted by stimulation in the omnipause region in monkey. Visual neuroscience. 1996; 13(6):1059-67. Epub Nov. 1, 1996. PubMed PMID: 8961536.

Keller EL, Gandhi NJ, Vijay Sekaran S. Activity in deep intermediate layer collicular neurons during interrupted saccades. Experimental brain research. 2000;130(2):227-37. Epub Feb. 15, 2000. PubMed PMID: 10672476.

Becker W. The neurobiology of saccadic eye movements. Metrics. Reviews of oculomotor research. 1989;3:13-67. Epub Jan. 1, 1989. PubMed PMID: 2486323.

Galvan A, Stauffer WR, Acker L, El-Shamayleh Y, Inoue KI, Ohayon S, et al. Nonhuman Primate Optogenetics: Recent Advances and Future Directions. The Journal of neuroscience : the official journal of the Society for Neuroscience. 2017;37(45): 10894-903 Epub Nov. 10, 2017. doi: 10.1523/jneurosci.1839-17.2017. PubMed PMID: 29118219; PubMed Central PMCID: PMCPMC5678022.

Grosenick L, Marshel JH, Deisseroth K. Closed-loop and activity-guided optogenetic control. Neuron. 2015;86(1):106-39. Epub Apr. 10, 2015. doi: 10.1016/j.neuron.2015.03.034. PubMed PMID: 25856490; PubMed Central PMCID: PMCPMC4775736.

El-Shamayleh Y, Kojima Y, Soetedjo R, Horwitz GD. Selective Optogenetic Control of Purkinje Cells in Monkey Cerebellum. Neuron. 2017;95(1):51-62.e4. Epub Jun. 27, 2017. doi: 10.1016/j.neuron.2017.06.002. PubMed PMID 28648497; PubMed Central Pmcid: PMCPMC5547905.

Scudder CA, Kaneko CS, Fuchs AF. The brainstem burst generator for saccadic eye movements: a modem synthesis. Experimental brain research. 2002;142(4):439-62. Epub Feb. 15, 2002. doi: 10.1007/s00221-001-0912-9. PubMed PMID: 11845241.

Hopp JJ, Fuchs AF. The characteristics and neuronal substrate of saccadic eye movement plasticity. Progress in neurobiology. 2004;72(1):27-53. Epub Mar. 17, 2004. doi: 10.1016/j.pneurobio. 2003.12.002. PubMed PMID: 15019175.

Soetedjo R, Kojima Y, Fuchs AF. How cerebellar motor learning keeps saccades accurate. Journal of neurophysiology 2019;121(6):2153-62. Epub Apr. 18, 2019. doi: 10.1152/jn.00781.2018. PubMed PMID: 30995136; PubMed Central PMCID: PMCPMC6620692.

Shadlen MN, Newsome WT. Neural basis of a perceptual decision in the parietal cortex (area LIP) of the rhesus monkey. Journal of neurophysiology. 2001;86(4):1916-36. Epub Oct. 16, 2001. doi: 10.1152/jn.2001.86.4.1916. PubMed PMID:11600651.

Camalier CR, Gotler A, Murthy A, Thompson KG, Logan GD, Palmeri TJ, et al. Dynamics of saccade target selection race model analysis of double step and search step saccade production in human and macaque. Vision research. 2007;47(16):2187-211. Epub Jul. 3, 2007. doi: 10.1016/j.visres.2007.04.021. PubMed PMID: 17604806; PubMed Central PMCID: PMCPMC2041801.

Gold JI, Shadlen MN. Representation of a perceptual decision in developing oculomotor commands. Nature. 2000;404 (6776):390-4. Epub 2000/04/04. doi: 10.1038/35006062. PubMed PMID: 10746726.

Robinson DA. A Method of Measuring Eye Movement Using a Scleral Search Coil in a Magnetic Field. IEEE transactions on bio-medical engineering. 1963;10:137-45. Epub Oct. 1, 1963. PubMed PMID: 14121113.

Fuchs AF, Robinson DA. A method for measuring horizontal and vertical eye movement chronically in the monkey. Journal of applied physiology. 1966;21(3):1068-70. Epub May 1, 1966. PubMed PMID: 4958032.

Judge SJ, Richmond BJ, Chu FC. Implantation of magnetic search coils for measurement of eye position: an improved method. Vision research. 1980;20(6):535-8. Epub Jan. 1, 1980. PubMed PMID: 6776685.

Houben MM, Goumans J, van der Steen J. Recording three-dimensional eye movements: scleral search coils versus video oculography. Investigative ophthalmology & visual science. 2006;47(1):179-87. Epub Dec. 31, 2005. doi: 10.1167/iovs.05-0234. PubMed PMID: 16384960.

Zuber BL, Semmlow JL, Stark L. Frequency characteristics of the saccadic eye movement. Biophysical journal. 1968;8(11):1288-98. Epub Nov. 1, 1968. doi: 10.1016/s0006-3495(68)86556-7. PubMed PMID: 5696212; PubMed Central PMCID: PMCPMC1367695.

Fuchs AF. Saccadic and smooth pursuit eye movements in the monkey. The Journal of physiology. 1967;191(3):609-31. Epub Aug. 1, 1967. PubMed PMID: 4963872; PubMed Central PMCID: PMCPMC1365495.

MacAskill MR, Anderson TJ. Eye movements in neurodegenerative diseases. Current Opinion in Neurology. 2016;29(1):61-8. doi: 10.1097/wco.0000000000000274. PubMed PMID: WOS:000369546400011.

Balandong RP, Ahmad RF, Saad MNM, Malik AS. A Review on EEG-Based Automatic Sleepiness Detection Systems for Driver, Ieee Access. 2018;6:22908-19. doi: 10.1109/access.2018.2811723. PubMed PMID: WOS:000432590200001.

Posner MI, Snyder CR, Davidson BJ. Attention and the detection of signals. Journal of experimental psychology General 1980;109(2):160.

Van Gog T, Scheiter K. Eye tracking as a tool to study and enhance multimedia learning. Elsevier; 2010.

Usui T, Tanimoto N, Ueki S, Miki A, Takagi M, Hasegawa S, et al. Night blindness with depolarizing pattern of ON/OFF response in electroretinogram: A case report. Documenta Ophthalmologica. 2005;111(1):15-21. doi: 10.1007/510633-005-3158-1. PubMed PMID: WOS:000236706200003.

Montagnese S, Amodio P, Morgan MY. Methods for diagnosing hepatic encephalopathy in patients with cirrhosis: A multidimensional approach. Metabolic Brain Disease. 2004;19(3-4):281-312. doi: 10.1023/B: MEBR.0000043977.11113.2a. PubMed PMID: WOS:000224325500013.

Paolozza A, Treit S, Beaulieu C, Reynolds JN. Diffusion tensor imaging of white matter and correlates to eye movement control and psychometric testing in children with prenatal alcohol exposure. Human brain mapping. 2017;38(1):444-56.

Grant MP, Cohen M, Petersen RB, Halmagyi GM, McDougall A, Tusa RJ, et al. Abnormal eye movements in Creutzfeldt-Jakob disease. Annals of neurology. 1993;34(2): 192-7. Epub Aug. 1, 1993. doi: 10.1002/ana.410340215. PubMed PMID: 8338343.

(56) References Cited

OTHER PUBLICATIONS

Rosenhall U, Johansson E, Gillberg C. Oculomotor findings in autistic children. The Journal of laryngology and otology. 1988;102(5):435-9. Epub May 1, 1988. doi: 10.1017/S0022215100105286. PubMed PMID: 3397639.

Jones GM, DeJong JD. Dynamic characteristics of saccadic eye movements in Parkinson's disease. Experimental neurology. 1971;31(1):17-31. Epub Apr. 1, 1971. doi: 10.1016/0014-4886(71)90173-7. PubMed PMID: 5554972.

Caslake R, Taylor K, Scott N, Harris C, Gordon J, Wilde K, et al. Age-, and gender-specific incidence of vascular parkinsonism, progressive supranuclear palsy, and parkinsonian-type multiple system atrophy in North East Scotland the PINE study. Parkinsonism & related disorders. 2014;20(8):834-9.

Ohta K, Tobinaga M, Hisako E, Ikeda T, Izumi A, Yonemochi Y, et al. Diagnosis of atypical type of progressive supranuclear palsy using IMP SPECT. Journal of the Neurological Sciences. 2017;381:593.

Chen K, Gao W, Emaminejad S, Kiriya D, Ota H, Nyein HYY, et al. Printed Carbon Nanotube Electronics and Sensor Systems. Advanced Materials. 2016;28(22):4397-414. doi: 10.1002/adma.201504958. PubMed PMID: WOS:000 3771 23500012.

Xu S, Zhang YH, Jia L, Mathewson KE, Jang KI, Kim J, et al. Soft Microfluidic Assemblies of Sensors, Circuits, and Radios for the Skin. Science. 2014;344(6179):70-4. doi: 10.1126/science.1250169. PubMed PMID: WOS:000333746100053.

Cai L, Song L, Luan PS, Zhang Q, Zhang N, Gao QQ, et al. Super-stretchable, Transparent Carbon Nanotube-Based Capacitive Strain Sensors for Human Motion Detection. Scientific Reports. 2013;3. doi: 10.1038/srep03048. PubMed PMID: WOS:000326094300002.

Kim SY, Park S, Park HW, Park DH, Jeong Y, Kim DH. Highly Sensitive and Multimodal All-Carbon Skin Sensors Capable of Simultaneously Detecting Tactile and Biological Stimuli. Advanced Materials. 2015;27(28):4178-85. doi 10.1002/adma.201501408. PubMed PMID: WOS:000358088400007.

Cheng Y, Wang RR, Sun J, Gao L. A Stretchable and Highly Sensitive Graphene-Based Fiber for Sensing Tensile Strain, Bending, and Torsion. Advanced Materials. 2015;27(45):7365-+. doi: 10.1002/adma.201503558. PubMed PMID: WOS:000367833200014.

Wei Y, Chen S, Dong XC, Lin Y, Liu L. Flexible piezoresistive sensors based on "dynamic bridging effect" of silver nanowires toward graphene. Carbon. 2017;113:395-403. doi: 10.1016/j.carbon.2016.11.027. PubMed PMID: WOS:000392686600046.

Pang Y, Tian H, Tao LQ, Li YX, Wang XF, Deng NQ, et al. Flexible, Highly Sensitive, and Wearable Pressure and Strain Sensors with Graphene Porous Network Structure. Acs Applied Materials & Interfaces. 2016;8(40):26458-62. doi: 10.1021/acsami.6b08172.

Lipomi DJ, Vosgueritchian M, Tee BCK, Hellstrom SL, Lee JA, Fox CH, et al. Skin-like pressure and strain sensors based on transparent elastic films of carbon nanotubes. Nature Nanotechnology. 2011;6(12):788-92. doi: 10.1038/nnano.2011.184. PubMed PMID: WOS:000298248300011.

Itakura N, Sakamoto K. A new method for calculating eye movement displacement from AC coupled electro-oculographic signals in head mounted eye-gaze input interfaces. Biomedical Signal Processing and Control. 2010;5(2):142-6. doi: 10.1016/j.bspc.2009.12.002. PubMed PMID: WQS:000277938800007.

Bonato P. Advances in wearable technology and applications in physical medicine and rehabilitation. Journal of NeuroEngineering and Rehabilitation. 2005;2(2):1–4.

Binkley PF, Frontera W, Standaert DG, Stein J. Predicting the potential of wearable technology—Physicians share their vision of future clinical applications of wearable technology, Ieee Engineering in Medicine and Biology Magazine. 2003;22(3):23-7. doi: 10.1109/memb.2003.1213623. PubMed PMID: WOS:000183765600009.

Frontera W. The importance of technology in rehabilitation. IEEE engineering in medicine and biology magazine : the quarterly magazine of the Engineering in Medicine & Biology Society. 2003;22(3). PubMed PMID: MEDLINE:12845814.

Hansen DW, Ji Q. In the eye of the beholder: A survey of models for eyes and gaze. IEEE transactions on pattern analysis and machine intelligence 2010;32(3):478-500.

Zhang J-Y, Lee GY, Cerwyn C, Yang JK, Fondio F, Kim JH, et al. Fracture-Induced Mechano-Electrical Sensitivities of Paper-Based Nanocomposites. Advanced Materials Technologies 2018;3(3):1700266.

Kahng S-J, Cerwyn C, Dincau BM, Kim J-H, Novosselov IV, Anantram M, et al. Nanoink Bridge-induced Capillary Pen Printing for Chemical Sensors. Nanotechnology. 2018.

Consejo A, Llorens-Quintana C, Bartuzel MM, Iskander DR, Rozema JJ. Rotation asymmetry of the human sclera. Acta ophthalmologica. 2019;97(2):e266-e70. Epub Aug. 28, 2018. doi: 10 1111/aos.13901. PubMed PMID: 30146759.

Wang D. Capacitive Sensing: Ins and Outs of Active Shielding. (Texas Instruments Inc, 2015).

Schultz AH. The size of the orbit and of the eye in primates. American Journal of Physical Anthropology. 1940;26(1):389-408. doi: 10.1002/ajpa.1330260138.

Brodie G, Jacob MV, Farrell P. Microwave and Radio-Frequency Technologies in Agriculture, An Introduction for Agriculturalists and Engineers: De Gruyter Open Ltd.; 2015.

Pauly H, Schwan HP. The dielectric properties of the bovine eye Lens,. IEEE Transactions on Bio-medical Engineering. 1964;BME-11(3):103.

Gabriel C, Gabriel S, Corthout E. The dielectric properties of biologic tissues: L Literature Survey. Phys Med Biol. 1996;41:2251.

Gabriel S, Lau RW, Gabriel C. The dielectric properties of biologic tissues: II. Measurement in the frequency range 10 Hz to 20 GHz. Phys Med Biol. 1996;41:2251.

Hershkovich HS, Urman N, Yesharim O, Naveh A, Bomzon Z. The dielectric properties of skin and their influence on the delivery of tumor treating fields to the torso: a study combining in vivo measurements with numerical simulations. Physics in Medicine and Biology. 2019;64(18). doi: 10.1088/1361-6560/ab33c6. PubMed PMID: WOS:000487116400003.

Martusevich AK, Galka AG, Krasnova SY, Yanin DV, Kostrov AV. Comparative study of dielectric properties of the skin of human and laboratory animals EPJ Web Conf. 2018;08004.

Maruyama Y, Kamata H, Watanabe S, Kita R, Shinyashiki N, Yagihara S. Electric-field penetration depth and dielectric spectroscopy observations of human skin. Version record online:. 2019.

Mayrovitz HN, Gildenberg SR, Spagna P, Killpack L, Altman DA. Characterizing the tissue dielectric constant of skin basal cell cancer lesions. Skin Research and Technology. 2018;24(4):686-91. doi: 10.1111/srt.12585. PubMed PMID: WOS:000446462500022.

Saviz M, Faraji-Dana R. A Theoretical Model for the Frequency-Dependent Dielectric Properties of Corneal Tissue at Microwave Frequencies. Progress in Electromagnetics Research-Pier. 2013;137:389-406. doi: 10.2528/pier12112510. PubMed PMID: WOS:000316931700023.

Li JF, Burke PJ. Measurement of the combined quantum and electrochemical capacitance of a carbon nanotube. Nature Communications. 2019;10. doi: 10.1038/S41467-019-11589-9 PubMed PMID: WOS:000480234500012.

Anantram MP, Lundstrom M, Nikonov D. Modeling of Nanoscale Devices. Proc IEEE 2008;96:1151.

Hetmaniuk U, Zhao Y, Anantram MP. A nested dissection approach to modeling transport in nanodevices: Algorithms and applications. International Journal for Numerical Methods in Engineering. 2013;95(7):587-607. doi: 10.1002/hme.4518. PubMed PMID: WOS:000321850300003.

Zhao Y, Hetmaniuk U, Patil SR, Qi J, Anantram MP. Nested dissection solver for transport in 3D nano-electronic devices. Journal of Computational Electronics. 2016;15(2):708-20. doi: 10.1007/s10825-015-0778-x. PubMed PMID: WOS:000375714500040.

Anantram MP, Govindan TR. Transmission through carbon nanotubes with polyhedral caps. Physical Review B. 2000;61(7):5020-5. doi: 10.1103/PhysRevB.61.5020. PubMed PMID: WOS:000085497200114.

Soetedjo R. Spatial updating of saccades: What do the superior colliculus and cerebellum do? Soc Neurosci Abstr. 2016.

Soetedjo R, Kaneko CR, Fuchs AF. Evidence that the superior colliculus participates in the feedback control of saccadic eye

(56) References Cited

OTHER PUBLICATIONS movements. Journal of neurophysiology. 2002;87(2):679-95. Epub Feb. 5, 2002. PubMed PMID: 11826037.

Collingridge DS. A Primer on Quantitized Data Analysis and Permutation Testing. Journal of Mixed Methods Research. 2013;7(1):81-97. doi: 10.1177/1558689812454457.

Pitman EJG. Significance Tests Which May be Applied to Samples From any Populations. Supplement to the Journal of the Royal Statistical Society. 1937;4(1):119-30. doi: 10.2307/2984124.

Fuchs AF, Scudder CA, Kaneko CR. Discharge patterns and recruitment order of identified motoneurons and internuclear neurons in the monkey abducens nucleus. Journal of neurophysiology. 1988;60(6):1874-95. Epub Dec. 1, 1988. doi: 10.1152/jn.1988.60.6.1874. PubMed PMID: 2466962.

Sylvestre PA, Cullen KE. Quantitative analysis of abducens neuron discharge dynamics during saccadic and slow eye movements. Journal of neurophysiology. 1999;82(5):2612-32. Epub Nov. 24, 1999. doi: 10.1152/jn.1999.82.5.2612. PubMed PMID: 10561431.

Kondo K, Watanabe K. A switched-capacitor interface for capacitive sensors with wide dynamic range. IEEE Transactions on Instrumentation and Measurement. 1989;38(3):736-9. doi: 10.1109/19.32183.

Pethig R. Dielectric Properties of Biological Materials: Biophysical and Medical Applications. IEEE Transactions on Electrical Insulation. 1987;EI-19(5):453.

Lee HB, Inoue S, Kim JH, Jeong M, Chung JH. Electrokinetic Behavior of Heat-Treated Mycobacterium Bacillus Calmette-Guerin Cells. Journal of Medical Devices—Transactions of the ASME. 2018;12(4). doi: 10.1115/1.4040677. PubMed PMID: WOS:000449533600009.
S I, HB L, AL B, KM W, JH K, KH L, et al. Dielectrophoretic characterization of antibiotic-treated *Mycobacterium tuberculosis* complex cells. Analytical Bioanalytical Chemistry 2015;407(25):7673-80.
Robinson FR, Soetedjo R, Noto C. Distinct short-term and long-term adaptation to reduce saccade size in monkey. Journal of neurophysiology. 2006;96(3):1030-41. Epub May 5, 2006. doi: 10.1152/jn.01151.2005. PubMed PMID: 16672299.
Faulkner L. Beyond the five-user assumption: Benefits of increased sample sizes in usability testing. Behavior Research Methods, Instruments, & Computers 2003;35(3):379-83.
Ten Harkel TC, Speksnijder CM, van der Heijden F, Beurskens CHG, Ingels KJAO, Maal TJJ. Depth accuracy of the RealSense F200: Low-cost 4D facial imaging. Scientific reports 2017;7(1):16263 doi: 10.1038/S41598-017-16608-7.
Ning HC, Han CC, Yuan CH. The Review of Applications and Measurements in Facial Electromyography. Journal of Medical and Biological Engineering. 2004;25:15-20.
MacKenzie IS. Evaluating eye tracking systems for computer input. In Gaze interaction and applications of eye tracking: Advances in assistive technologies: IGI Global; 2012.
Wedel M, Pieters R. A review of eye-tracking research in marketing. Review of marketing research. 2008;4:123-47.
Pieters R, Warlop L. Visual attention during brand choice: The impact of time pressure and task motivation. International Journal of Research in Marketing. 1999;16(1):1-16. doi: 10.1016/s0167-8116(98)00022-6. PubMed PMID: WOS:00007841 2800001.
Brown DA, Kim J-H, Lee H-B, Fotouhi G, Lee K-H, Liu WK, et al. Electric Field Guided Assembly of One-Dimensional Nanostructures for High Performance Sensors. Sensors. 2012;12(5):5725-51. doi: 10.3390/s120505725. PubMed PMID: WOS:000304539200031.
Holtz J. Tissue paper sensors show promise for health care, entertainment, robotics University of Washington2018.
Yeo WH, Chung JH, Liu YL, Lee KH. Size-Specific Concentration of DNA to a Nanostructured Tip Using Dielectrophoresis and Capillary Action. Journal of Physical Chemistry B. 2009;113(31): 10849-58. doi: 10.1021/ip900618t. PubMed PMID: WOS:000268479000040.
Yeo WH, Liu S, Chung JH, Liu YL, Lee KH. Rapid detection of *Mycobacterium tuberculosis* cells by using microtipbased immunoassay. Analytical and Bioanalytical Chemistry. 2009;393(6-7): 1593-600. doi: 10.1007/s00216-008-2591-x. PubMed PMID: WOS:000263826100007.
Yeo W-H, Chou F-L, Fotouhi G, Oh K, Stevens BT, Tseng H-Y, et al. Size-selective immunofluorescence of *Mycobacterium tuberculosis* cells by capillary—and viscous forces. Lab on a Chip. 2010;10(22):3178-81. doi: 10.1039/c01c00077a. PubMed PMID: WOS:000283600900020.
Kalyanasundaram D, Inoue S, Kim J-H, Lee H-B, Kawabata Z, Yeo W-H, et al. Electric field-induced concentration and capture of DNA onto microtips. Microfluidics and Nanofluidics. 2012;13(2):217-25. doi: 10.1007/s10404-012-0956-0. PubMed PMID: WOS:000308821300003.
Kim J-H, Yeo W-H, Shu Z, Soelberg SD, Inoue S, Kalyanasundaram D, et al. Immunosensor towards low-cost, rapid diagnosis of tuberculosis. Lab on a Chip. 2012;12(8):1437-40. doi: 10.1039/c2lc21131a. PubMed PMID: WOS:000301986500006.
Kopacz AM, Yeo W-H, Chung J-H, Liu WK. Nanoscale sensor analysis using the immersed molecular electrokinetic finite element method. Nanoscale. 2012;4(16):5189-94. doi: 10.1039/c2nr31279d. PubMed PMID: WOS:000306855500050.
Yeo W-H, Kopacz AM, Kim J-H, Chen X, Wu J, Gao D, et al. Dielectrophoretic concentration of low-abundance nanoparticles using a nanostructured tip. Nanotechnology. 2012;23(48). doi: 10.1088/0957-4484/23/48/485707. PubMed PMID: WOS:000311138100042.
Kalyanasundaram D, Kim JH, Yeo WH, Oh K, Lee KH, Kim MH, et al. Rapid extraction and preservation of genomic DNA from human samples. Analytical and Bioanalytical Chemistry. 2013;405(6): 1977-83. doi: 10.1007/s00216-012-6637-8. PubMed PMID: WOS:000314681000020.
Kalyanasundaram D, Kim J-H, Fotouhi G, Lee H-B, Hiraiwa M, Oh K, et al. Nanotips for single-step preparation of DNA for qPCR analysis. Analyst. 2013;138:3135-8.
Kim J-H, Hiraiwa M, Lee H-B, Lee K-H, Cangelosi GA, Chung J-H. Electrolyte-free amperometric immunosensor using a dendritic nanotip. Rsc Advances. 2013;3(13):4281-7. doi: 10.1039/c3ra40262b. PubMed PMID: WOS:000315818200026.
Yeo WH, Lee HB, Kim JH, Lee KH, Chung JH. Nanotip analysis for dielectrophoretic concentration of nanosized viral particles. Nanotechnology. 2013;24(18). doi: 10.1088/0957-4484/24/18/185502. PubMed PMID WOS:000317468700010.
Inoue S, Shu Z, Kim J-H, Hiraiwa M, Lakley A, Weigel K, et al. Semi-Automated, Occupationally Safe mmunofluorescence Microtip Sensor for Rapid Detection of *Mycobacterium* Cells in Sputum. Plos One. 2014;9(1):e86018.
Kim J-H, Inoue S, Cangelosi GA, Lee K-H, Chung J-H. Study of Specific Capture of Target Bacteria onto Sensor Surface for Disease Diagnosis. Journal of Micromechanics and Microengineering. 2014;24:045009.
Hiraiwa M, Kim JH, Lee HB, Inoue S, Becker AL, Weigel KM, et al. Amperometric immunosensor for rapid detection of *Mycobacterium tuberculosis*. Journal of Micromechanics and Microengineering. 2015;25(5). doi: 10.1088/0960-1317/25/5/055013. PubMed PMID: WOS:000354802200014.
Zhao YQ, Wan ZN, Hetmanuik U, Anantram MP. Negative Differential Resistance in Graphene Boron Nitride Heterostructure Controlled by Twist and Phonon-Scattering, Ieee Electron Device Letters. 2016;37(9):1242-5. doi: 10.1109/led.2016.2595522. PubMed PMID: WOS:000383099400043.
Hetmaniuk U, Ji D, Zhao YQ, Anantram MP. A Reduced-Order Method for Coherent Transport Using Green's Functions, Ieee Transactions on Electron Devices. 2015;62(3):736-42. doi: 10.1109/ted.2015.2395420. PubMed PMID: WOS:000350332000007.
Jain N, Yang F, Jacobs-Gedrim RB, Xu X, Anantram MP, Yu B. Extenuated interlayer scattering in double-layered graphene/hexagonal boron nitride heterostructure. Carbon. 2018;126:17-22. doi: 10.1016/j.carbon.2017.09.074. PubMed PMID: WOS:000415319700003.
Shiri D, Rabbani MG, Qi JQ, Buin AK, Anantram MP. Photo absorption enhancement in strained silicon nanowires: An atomistic study. Journal of Applied Physics. 2017;122(3). doi: 10.1063/1.4993587. PubMed PMID: WOS:000406128800016.

(56) References Cited

OTHER PUBLICATIONS

Shiri D, Verma A, Nekovei R, Isacsson A, Selvakumar CR, Anantram MP. Gunn-Hilsum Effect in Mechanically Strained Silicon Nanowires: Tunable Negative Differential Resistance. Scientific Reports. 2018;8. doi: 10.1038/s41598-018-24387-y. PubMed PMID: WOS:000430382700011.

Zhao Y, Wan Z, Xu X, Patil SR, Hetmaniuk U, Anantram MP. A modeling study of mechanisms for ndr in graphene-bn-graphene heterostructures. IEEE Nanotechnology Materials and Devices Conference (NMDC). 2015.

Kojima Y, Soetedjo R. Elimination of the error signal in the superior colliculus impairs saccade motor learning. Proceedings of the National Academy of Sciences of the United States of America. 2018;115(38):E8987-E95. doi 10.1073/pnas.1806215115. PubMed PMID: WOS:000447224900019.

Soetedjo R. Signals driving the adaptation of saccades that require spatial updating. Journal of Neurophysiology. 2018;120(2):525-38. doi: 10.1152/jn.00075.2018. PubMed PMID: WOS:000441195200013.

Avanzini, G., Girotti, F., Caraceni, T., Spreafico, R., 1979. Oculomotor disorders in Huntington's chorea. Journal of neurology, neurosurgery, and psychiatry 42(7), 581-589.

Becker, W., 1989. The neurobiology of saccadic eye movements. Metrics. Reviews of oculomotor research 3, 13-67.

Dichiara, A.B., Song, A., Goodman, S.M., He, D., Bai, J., 2017. Smart papers comprising carbon nanotubes and cellulose microfibers for multifunctional sensing applications. Journal of Materials Chemistry A 5(38), 20161-20169.

Golparvar, A.J., Yapici, M.K., 2021. Toward graphene textiles in wearable eye tracking systems for human-machine interaction. Beilstein Journal of Nanotechnology 12, 180-189.

Jia, Y., Tyler, C.W., 2019. Measurement of saccadic eye movements by electrooculography for simultaneous EEG recording. Behavior Research Methods 51(5), 2139-2151.

Kim, N.I., Chen, J., Wang, W.J., Moradnia, M., Pouladi, S., Kwon, M.K., Kim, J.Y., Li, X.H., Ryou, J.H., 2021. Highly-Sensitive Skin-Attachable Eye-Movement Sensor Using Flexible Nonhazardous Piezoelectric Thin Film. Advanced Functional Materials 31(8).

Lee, S., Hinchet, R., Lee, Y., Yang, Y., Lin, Z.H., Ardila, G., Montes, L., Mouis, M., Wang, Z.L., 2014. Ultrathin Nanogenerators as Self-Powered/Active Skin Sensors for Tracking Eye Ball Motion. Advanced Functional Materials 24(8), 1163-1168.

Ran, Q., Chen, J., Li, C., Wen, L., Yue, F.G., Shu, T.S., Mi, J.X., Wang, G.X., Zhang, L., Gao, D., Zhang, D., 2017. Abnormal amplitude of low-frequency fluctuations associated with rapid-eye movement in chronic primary insomnia patients. Oncotarget 8(49), 84877-84888.

Rosenhall, U., Johansson, E., Gillberg, C., 1988. Oculomotor findings in autistic children. The Journal of laryngology and otology 102(5), 435-439.

Steele, J.C., Richardson, J.C., Olszewski, J., 1964. Progressive supranuclear palsy: a heterogeneous Regeneration involving the brain stem, basal ganglia and cerebellum with vertical gaze and pseudobulbar palsy, nuchal dystonia and dementia. Archives of neurology 10(4), 333-359.

Zhang, J.Y., Goodman, S.M., Wise, HG, Dichiara, A.B., Chung, J.H., 2021. Electromechanical Coupling of Isotropic Fibrous Networks with Tailored Auxetic Behavior Induced by Water-Printing under Tension. Journal of Materials Chemistry C DOI: 10.1039/D0TC05526C.

* cited by examiner

1. CPC paper (1x5 mm²)
2. Silver electrodes
3. Water print
4. Fracture
PF
PH
PR
5. PET lamination
*FIG. 4A*
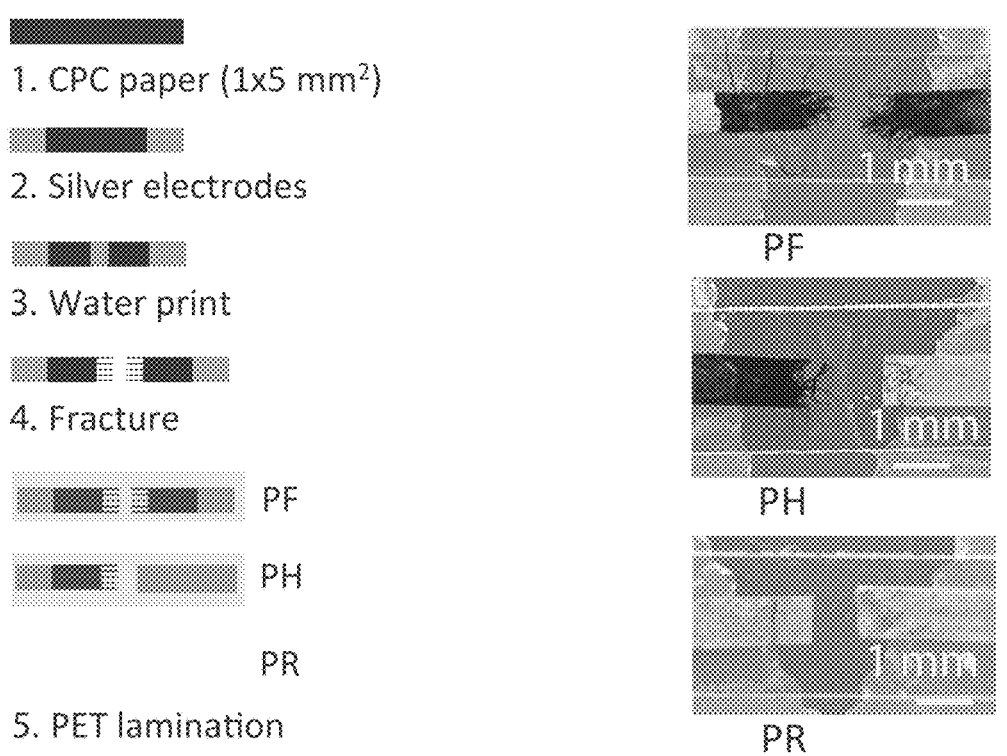
*FIG. 4B*
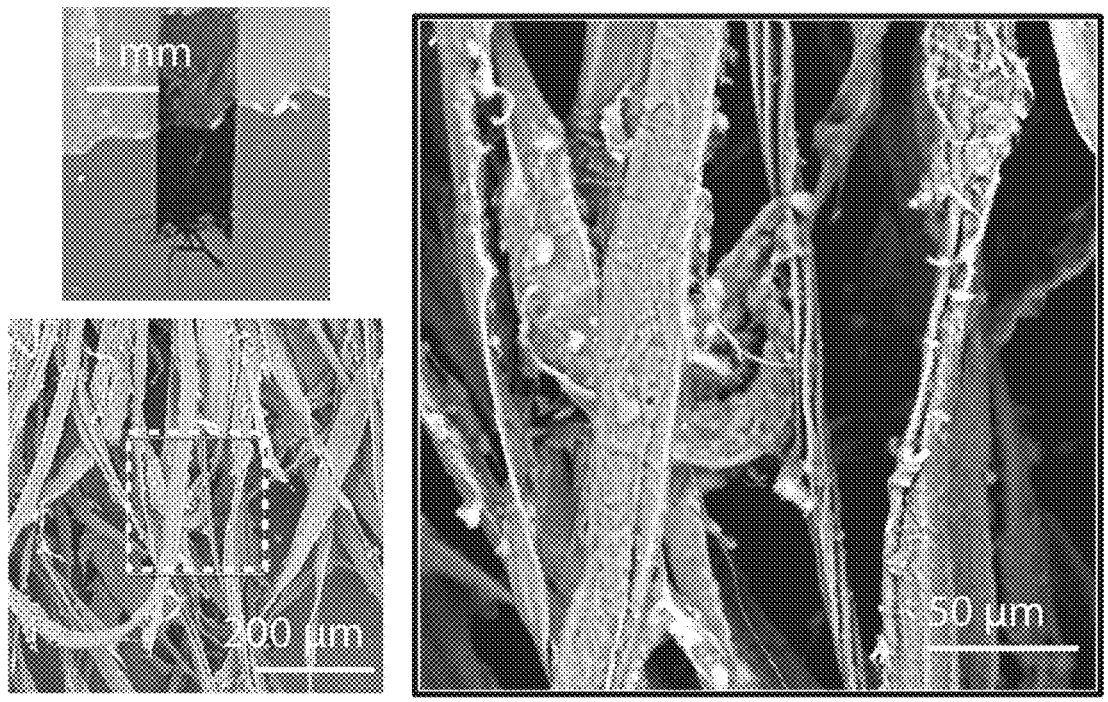
*FIG. 4C*

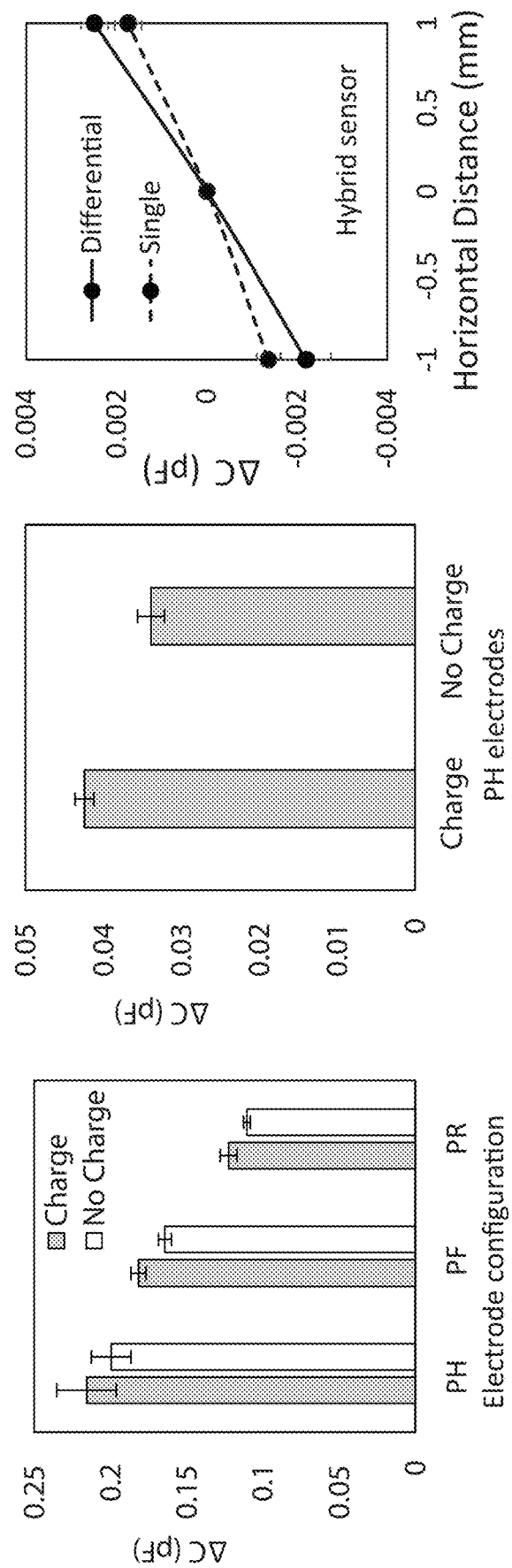
*FIG. 4F*  *FIG. 4G*  *FIG. 4H*

CAPACITANCE-BASED EYE TRACKER

CROSS-REFERENCE TO RELATED APPLICATION

This application claims the benefit of U.S. Provisional Application 63/179,045, filed Apr. 23, 2021, the disclosure of which is hereby incorporated by reference in its entirety.

STATEMENT OF GOVERNMENT LICENSE RIGHTS

This invention was made with Government support under Grant No. R21 EY031768 awarded by the National Institutes of Health and under Grant No. 1927623 by the Advanced Manufacturing Program of National Science Foundation. The Government has certain rights in the invention.

BACKGROUND

Wearable sensors have been made flexible, resilient, and small in size. The wearable sensors, especially for heartbeat, foot pressure, and skin movement monitoring directly impact sports medicine and rehabilitation. However, a wearable sensor to measure eye movement accurately and non-invasively is an open problem. Current methods to monitor eye movement are either bulky or invasive in nature.

These methods include: (i) An ultrathin piezoelectric nanogenerator attached to the eyelid generates an output voltage depending on the motion of an eyeball. This technology is in its initial phases (ii) A scleral coil that is invasively placed. The magnitude of the induced voltage is determined by the angles of the scleral coils and the magnetic flux. This procedure may not be adoptable by the general population due to its highly invasive nature. (iii) A capacitive sensor array to determine eye gaze detection. The movement of the eyeballs, muscles, and eyelids induce a change in the capacitance of a capacitor placed at a fixed point near the eye. However, the sensitivity was insufficient for precise measurement for eye movement. (iv) A camera-based desktop eye-tracking system is the major workhorse for many applications. However, this system is bulky, not portable, does not offer real-time data analysis, and requires post-processing of the stored datasets.

There is a lack of accurate eye trackers for diagnosing neurological disorder: In most ambulatory clinics, the physicians evaluate eye movement problems by naked eye. This technique is inaccurate and likely to lead to a wrong diagnosis. Additionally, conventional eye trackers are bulky, expensive, and require a long setup time. To render current camera-based systems applicable to disease diagnosis, significant improvements in hardware and software are needed. Using eye-tracking sensors in laboratory or clinical settings has been challenging due to the short visits of patients, low availability of equipment, and the requirement for highly trained medical technicians. Therefore, current eye monitoring sensors are inadequate for clinical tasks.

The challenges in the development of a robust solution include: (i) availability of miniature high-fidelity sensors and electronics for real-time signal processing, (ii) wearable platform that can account for subject's facial anatomy and minimize the effects of subject's movement on measurement quality, and (iii) inadequate data analysis algorithms and measurement calibration. Due to the challenges, the collected data may not reflect the natural daily eye movement, which may lead to false diagnosis.

Accordingly, non-invasive, high fidelity eye trackers and methods of use are needed.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, an eye-tracking system, including at least one vertical capacitance sensor, configured to measure the vertical position of a cornea of a user's eye by sensing a position of an eyelid of the user; and at least one horizontal capacitance sensor, configured to measure the horizontal position of the cornea of the user's eye by sensing a position of the user's eyeball is disclosed.

In another aspect, an eye-tracking system including an article including a left side and a right side, a first vertical sensor attached to the right side of the article, a second vertical sensor attached to the left side of the article, a first horizontal sensor attached to the right side of the article; and a second horizontal sensor attached to the left side of the article, wherein the first vertical sensor and the first horizontal sensor are configured to measure a vertical position and a horizontal position, respectively, of a cornea of a user's right eye by sensing a position of a right eyelid of the user and the user's right eyeball, and wherein the second vertical sensor and the second horizontal sensor are configured to measure a vertical position and a horizontal position, respectively, of a cornea of a user's left eye by sensing a position of a left eyelid of the user and the user's left eyeball, so that both a user's right eye movements and left eye movements are sensed simultaneously is disclosed.

In yet another aspect, a method of tracking a position of at least one eye of a user, including mounting an eye-tracking system according to any of the preceding claims to the user; and measuring capacitance from the at least one vertical sensor and the at least one horizontal sensor is disclosed

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 4A is an example of sensor fabrication, in accordance with the present technology;

FIG. 4B is an illustration of example sensor configurations, in accordance with the present technology;

FIG. 4C is an optical and SEM image of an example sensor, in accordance with the present technology;

FIG. 4F is a graph showing the change in capacitance for different sensor configurations, in accordance with the present technology;

FIG. 4G is a graph showing the change in capacitance for different sensor configurations without moving a face, in accordance with the present technology;

FIG. 4H is a comparison for the change of capacitance for single and differential capacitive measurement, in accordance with the present technology;

DETAILED DESCRIPTION

Described herein is a wearable sensing platform made of, in some embodiments, carbon nanotube-paper composites (CPC) to measure tiny changes in system capacitance with a thin film format. To replace the current camera-based system, CPC-capacitive sensors track eyeball movement and monitor eyelid movement, e.g., blinks. In some embodiments, the sensors are composed of multi-walled carbon nanotubes (MWCNTs) embedded in a micro cellulose fiber matrix. MWCNTs may be randomly distributed throughout the fiber network. When the matrix is fractured, the separated MWCNTs form a capacitance network. Electrical termination forms a capacitance along the crack. The capacitive sensors are packaged for non-contact measurement of the capacitance due to eyeball movement. The sensors use low-power electronics and can be integrated with any number of eye-tracking form factors.

Also described herein is a miniaturized wearable capacitive sensor made of a pair of asymmetric electrodes; one being carbon nanotube paper composite (CPC) fibers, and the other being a rectangular metal electrode. The capacitive interaction between asymmetric electrodes and a spherical eyeball is analyzed by numerical study. Using a face simulator, both single- and differential capacitive measurements are characterized to correlate eyeball movement and capacitive signal changes in terms of proximity, geometry, and human body charge. Based on the interaction study, multiple sensor locations were tested to find the optimal sensor locations for tracking the human eyeball. Vertical and horizontal eye movements were compared to those produced by a commercial eye tracker. The prototype eye tracker is demonstrated for smooth-pursuit eye-movement tracking, human-machine interface, and closed-eye movement monitoring. The proposed capacitive sensing device allows for unhindered eyesight while reducing parasitic capacitance using a minimal number of capacitive sensors. The wearable eye-tracker, in some embodiments, is useful for human-machine interface, cognitive monitoring, neuroscience research, and rehabilitation.

In some embodiments, two pairs of sensors are placed onto eyeglasses. These sensors are configured to test the eye movement of a human subject. In one example, the sensors measured the eye movement of a human subject who was directed to move their eye left-right and up-down. Analog Devices (Norwood, Mass.) AD7746 capacitance to digital converter evaluation board may be used for the measurement. The capacitance may be measured by a differential method. In some embodiments, the sensors L and R are paired for leftward-rightward movements, and the sensors U and D are paired for upward/downward movements. The measurement may be performed at a sampling rate of 16 Hz without shielding the parasitic capacitance. In one embodiment, the detected capacitance changes were 20-30 fF. The sensitivity and accuracy may be increased based on the sensor-eye interaction model.

Figure 1A:
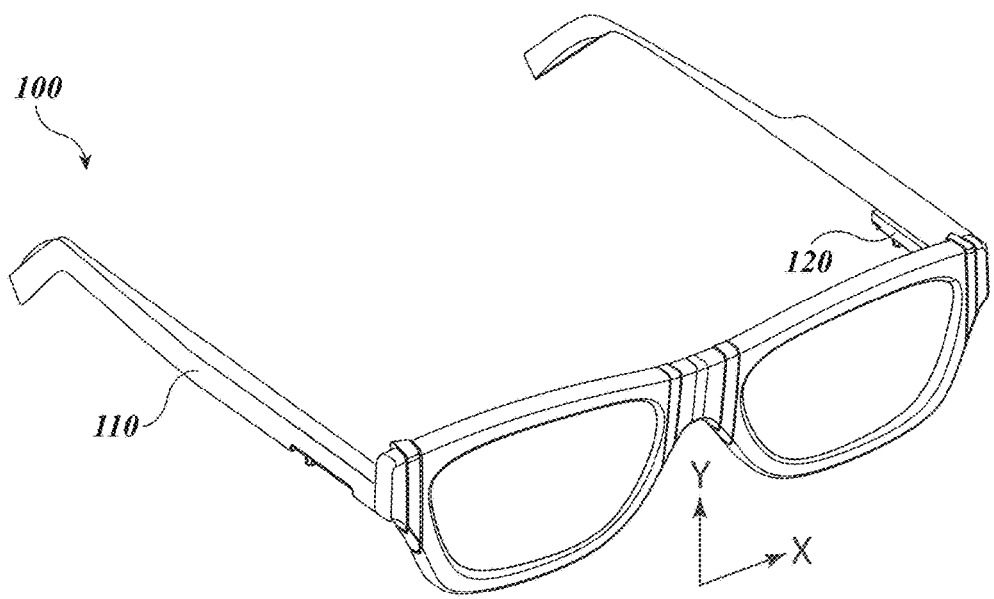
FIG. 1A is an example eye-tracker, in accordance with the present technology.

FIG. 1A is an example eye-tracker, in accordance with the present technology. The wearable eye tracker 100 may take the form of an eyeglass frame with integrated capacitive sensors, but in other embodiments, the eye tracker may be monocular or binocular lenses, an eye mask, goggles, or a mechanical support or adjustable ring configured to suspend the sensors in space above the eye. The small form factor of the sensors also allows for integration into existing headgears, such as virtual reality (VR) headsets. In some embodiments, to fit individual face shapes, malleable mounts are used to adjust the sensor location and distance, as shown in FIG. 8B. The geometry of the designed sensor may have 1×5 mm$^2$ area with 0.1 mm thickness.

Figure 1B:
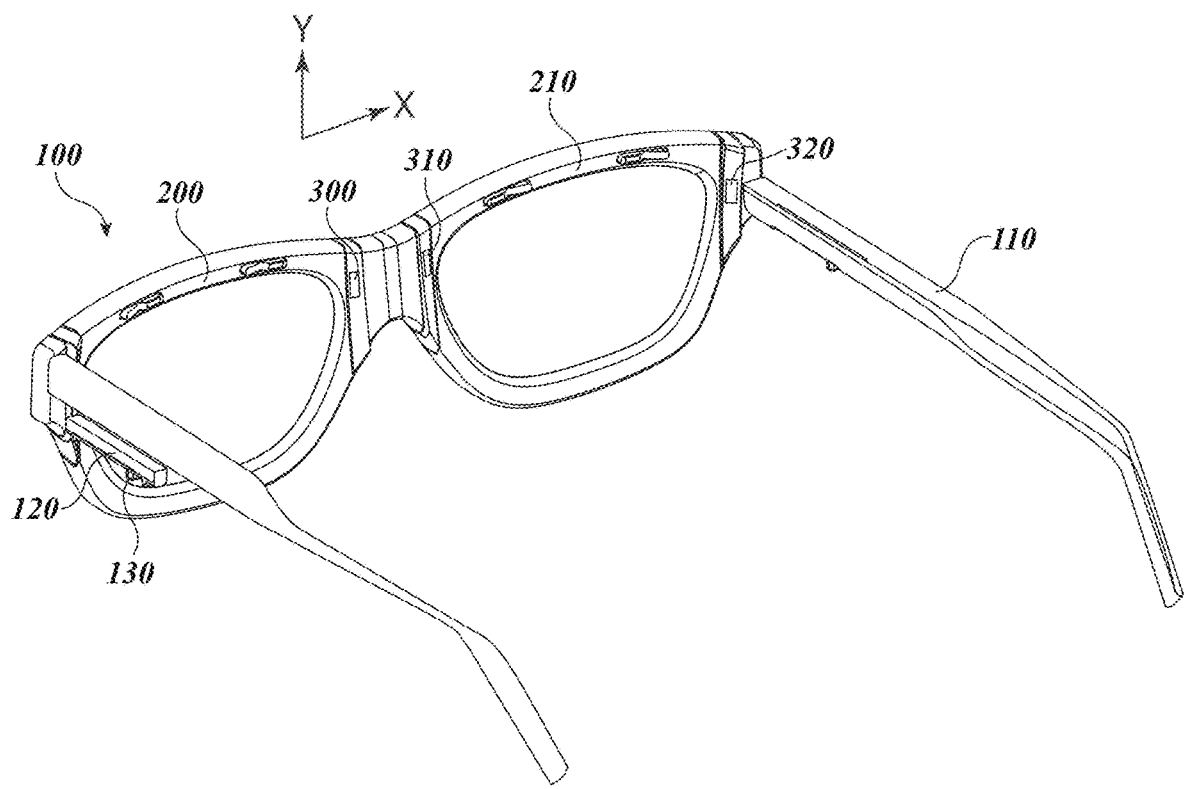
FIG. 1B is an example location of sensors on an eye-tracker, in accordance with the present technology.

In some embodiments, the wearable eye-tracker 100 may include at least one vertical sensor and at least one horizontal sensor, as described and shown in FIG. 1B.

In some embodiments, the wearable eye-tracker 100 may include an article 110 for securing the capacitive sensors. In some embodiments, the article may be monocular or binocular lenses, eyeglass frames, an eye mask, goggles, or a mechanical support or adjustable ring configured to suspend the sensors in space above the eye.

In some embodiments, the eye-tracker 100 may also include a processor 120 configured to configured to process the measurement signals and provide an output indicative of a position of the user's eye. In some embodiments, the processor is configured to execute instructions to apply machine learning and/or artificial intelligence to provide the output indicative of the position of the user's eye. In some embodiments, the processor includes an electronic control unit, configured to control and receive measurement signals from the at least one vertical sensor and the at least one horizontal sensor. In some embodiments, the electronic control unit may be a separate component of the eye-tracker. While the processor 120 is shown on the side of the article 110, the processor 120 may be in any location, including connected to the capacitive sensors with a wired connection. In some embodiments, the processor 120 may not be located on the article 110.

In some embodiments, the eye-tracker 100 may further include an IR camera system in combination with horizontal and vertical capacitive sensors to synchronously acquire data of higher sensitivity and accuracy In operation, for capacitive measurement, the asymmetry in the geometrical shape of the eyeball near the scleral-corneal junction causes the distance change of the eyeball surface to the sensor under rotation. The distance change affects the fringing electric field, which in turn changes the capacitance, as shown in FIG. 1D.

FIG. 1B is an example location of sensors on an eye-tracker, in accordance with the present technology. The sensors were adjusted multiple times to determine an optimal distance between the sensor and the human eyeball. As shown, in some embodiments, the sensors 200, 210, 300, 310, and 320 are placed inside the frame of the article 110, on the side facing a user.

In some embodiments, the eye tracker 100 includes at least one vertical capacitance sensor 200, 210, configured to measure the vertical position of a cornea of a user's eye by sensing a position of an eyelid of the user, and at least one horizontal capacitance sensor, 300, 310, configured to measure the horizontal position of the cornea of the user's eye by sensing a position of the user's eyeball. In some embodiments, there may also be a second vertical sensor (not pictured in FIG. 1B) and a second horizontal sensor 320. In some embodiments, each lens of the article 110 includes at least one vertical sensor 200, 210, and at least one horizontal sensor 300, 310. In some embodiments, each lens includes at least one horizontal sensor 300, 310 and a second horizontal sensor 320. While the second horizontal sensor of the left lens of article 110 is obscured, it should be appreciated that it is located at the same relative position of second horizontal sensor 320, but on the left lens (as shown in FIG. 8B). In some embodiments, the total number of horizontal sensors 300, 310, 320 is 2 or fewer. In some embodiments, the total number of vertical sensors 200, 210 is 2 or fewer.

In some embodiments, the article 110 includes a left side and a right side. In some embodiments, the left side of the article 110 may be a left lens of a pair of eyeglasses and the right side of the article 110 may be a right lens of the pair of eyeglasses, such as illustrated in FIG. 1B. In some embodiments, the right side and the left side of the article 110 may be the right and left side of a sleep mask. In some embodiments, the eye-tracking system includes a first vertical sensor 200 attached to the right side of the article, a second vertical sensor 210 attached to the left side of the article, a first horizontal sensor 300 attached to the right side of the article and a second horizontal sensor 310 attached to the left side of the article.

In operation, the first vertical sensor 200 and the first horizontal sensor 300 are configured to measure a vertical position and a horizontal position, respectively, of a cornea of a user's right eye by sensing a position of a right eyelid of the user and the user's right eyeball. Similarly, the second vertical sensor 210 and the second horizontal sensor 310 are configured to measure a vertical position and a horizontal position, respectively, of a cornea of a user's left eye by sensing a position of a left eyelid of the user and the user's left eyeball, so that both a user's right eye movements and left eye movements are sensed simultaneously.

In some embodiments, the eye-tracking system 100 further includes an electronic ground 130 configured to electrically connect the eye-tracking system to a body of the user in order to increase the capacitance change detected by the vertical and horizontal capacitive sensors. While the electronic ground 130 is illustrated to be a part of the processor 120, in some embodiments, the electronic ground is a separate component. In some embodiments, the electronic ground is not attached to the article 110.

In operation, and as described in further detail herein, the at least one vertical capacitance sensor 200, 210 and the second vertical capacitance sensor (not pictured in FIG. 1B) operate using differential measurement to measure the vertical position of the cornea of the user's eye. Similarly, the at least one horizontal capacitance sensor 300, 310 and the second horizontal capacitance sensor 320 operate using differential measurement to measure the horizontal position of the cornea of the user's eye. In some embodiments, the horizontal and vertical sensors are rotated up to 45 degrees clockwise to increase sensitivity to eye movement.

Figure 1C:
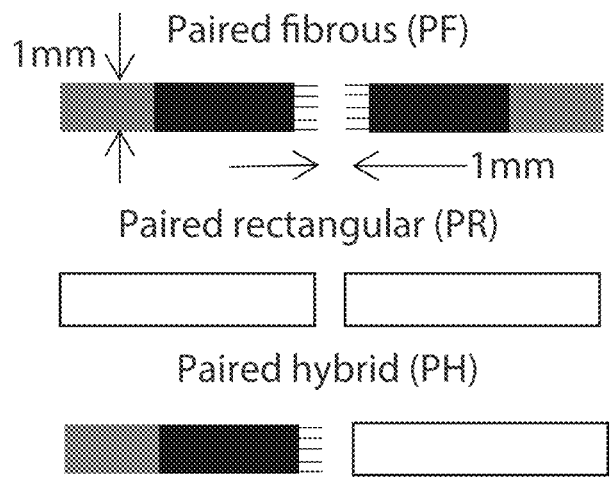
FIG. 1C is an illustration of example sensor configurations, in accordance with the present technology.
Figure 1D:
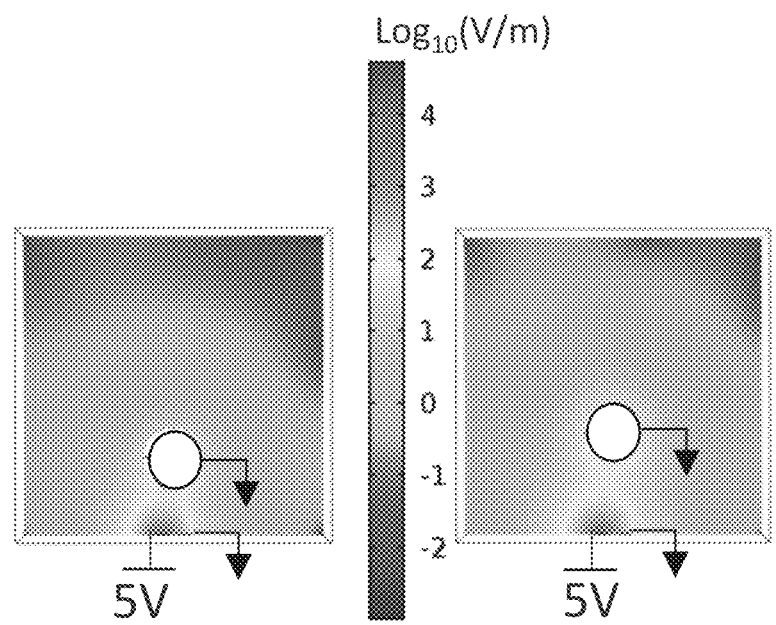
FIG. 1D is a graph of example electric field distribution with a spherical object at different distances from an example sensor, in accordance with the present technology.

FIG. 1C is an illustration of example sensor configurations, in accordance with the present technology. The capacitive sensors, such as at least one vertical sensor 200, 210 and at least one horizontal capacitive sensor 300, 310 as shown in FIG. 1B, may be comprised of paired fibrous (PF), paired rectangular (PR), and/or paired hybrid (PH) electrodes. In some embodiments, the sensors have different electrode combinations. Three different electrode combinations were tested for sensitivity evaluation by numerical computation. One was paired fibrous (PF) electrodes, another was paired rectangular (PR) electrodes, and the last one was paired hybrid (PH) electrodes consisting of fibrous and rectangular electrodes.

In some embodiments, the at least one vertical sensor and the at least one horizontal sensor are each comprised of two electrodes. In some embodiments, the one or more vertical capacitance sensors are a carbon nanotube paper composite sensor. In some embodiments, the vertical capacitance sensors are further comprised of multi-walled carbon nanotubes embedded in the template material, wherein the template material comprises a micro cellulose fiber matrix template material. In some embodiments, the vertical capacitance sensors are comprised of a template material comprising at least a first electrode, and a second electrode. The first electrode may be a carbon-nanotube paper composite electrode, and the second electrode may be a rectangular electrode. In some embodiments, the first electrode is a first carbon nanotube paper composite electrode, and the second electrode is a second carbon nanotube paper composite electrode.

Further, in some embodiments, the one or more horizontal capacitance sensors is a carbon nanotube paper composite sensor. In some embodiments, the horizontal capacitance sensors are further comprised of multi-walled carbon nanotubes embedded in the template material, wherein the template material comprises a micro cellulose fiber matrix template material. The one or more horizontal capacitance sensors may be comprised of a template material comprising at least a first electrode, and a second electrode. The first electrode may be a carbon-nanotube paper composite electrode, and the second electrode may be a rectangular electrode. Still, in some embodiments, the first electrode is a first carbon nanotube paper composite electrode, and the second electrode is a second carbon nanotube paper composite electrode.

FIG. 1D is a graph of an example electric field distribution with a spherical object at different distances from an example PH sensor, in accordance with the present technology. The key shows the $\text{Log}_{10}$, in V/m. On the right side is an electric field generated by a sensor 4 mm from a spherical object. On the left side is an electric field generated by a sensor 6 mm from a spherical object. The circle represents the spherical object. At the bottom of the square field is the electrode, to which 5V were applied.

The capacitive sensitivity is defined as the ratio of capacitance change to distance change ($\Delta C/\Delta d$), where C is the capacitance and d is the distance between a sensor to an eyeball. The gap size between the electrodes was 1 mm. A 5 mm-diameter sphere, representing an eyeball, floated in the center. A 5V AC potential with 25 kHz frequency was applied between the two electrodes. For hybrid electrodes, 5V was applied to the fiber electrode while the rectangular metal electrode was grounded. The relative permittivity of a spherical object was 80. When a voltage is applied between the two CPC sides, a fringing electric field is generated. Because the electric field is inversely proportional to the diameter of MWCNTs, the field strength significantly increases as the diameter decreases to 10 nm.

Figure 1E:
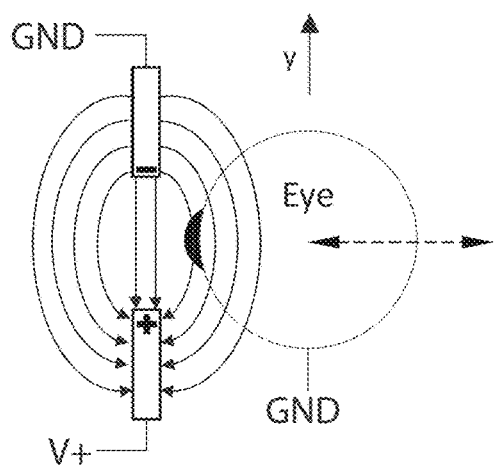
FIG. 1E is an illustration of a single capacitance measurement, in accordance with the present technology.
Figure 1F:
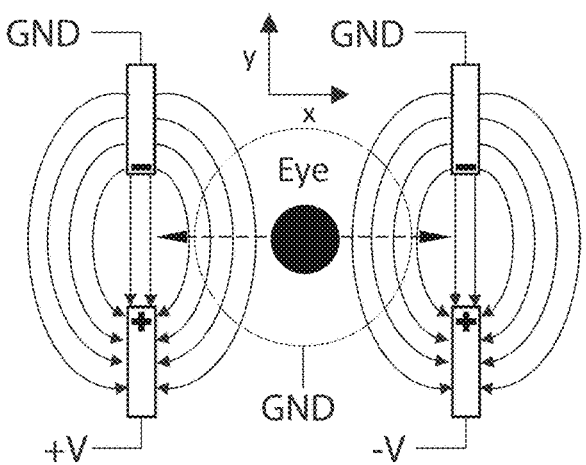
FIG. 1F is an illustration of a differential capacitance measurement, in accordance with the present technology.

FIG. 1E is an illustration of a single capacitance measurement, in accordance with the present technology. FIG. 1F is an illustration of a differential capacitance measurement, in accordance with the present technology. The $\Delta C$ due to the fringing electric field could be computed by either single (FIG. 1E) or differential methods (FIG. 1F). "GND" in both FIGS. 1E and 1F represents the ground.

In operation, the single method (FIG. 1E) was convenient but suffered from the nonlinear relationship between capacitance and rotation angle. The differential method applied AC voltage 180° out of phase to the second sensor. The differential method doubled the sensitivity, canceled the nonlinearity, and, therefore, produced a more linear relationship between capacitance and rotation angle.

Figure 1G:
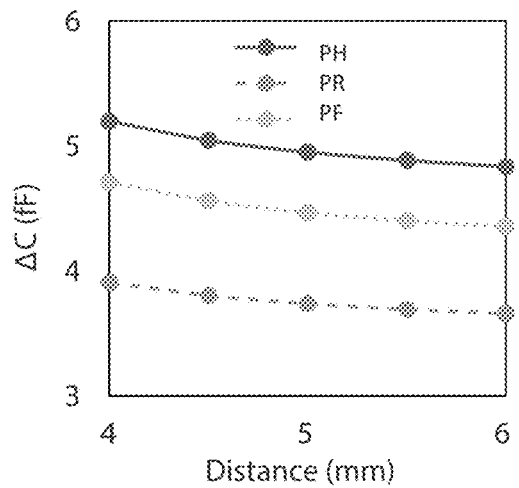
FIG. 1G is a graph of change in capacitance for different sensor configurations, in accordance with the present technology.

FIG. 1G is a graph of change in capacitance for different sensor configurations, in accordance with the present technology. On the vertical axis is the change in capacitance ($\Delta C$) in Ff. On the horizontal axis is the distance in mm.

The $\Delta C$ of PF, PR, and RH sensor capacitances for the distance between 4 and 6 mm to a target sphere (as shown in FIG. 1D) are graphed. Among the sensors, the PH electrodes showed the highest $\Delta C$ followed by those of PF and PR electrodes.

Figure 1H:
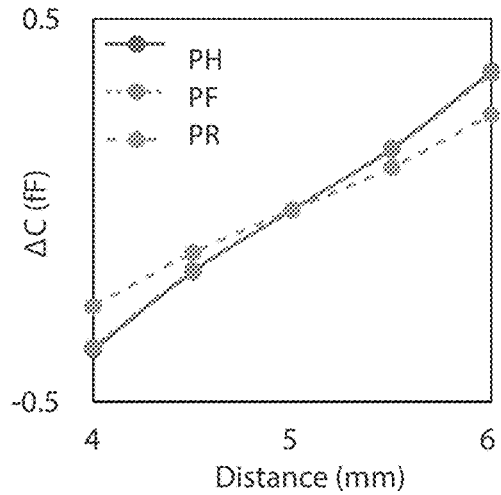
FIG. 1H is a graph of change in differential capacitance for different sensor configurations, in accordance with the present technology.

FIG. 1H is a graph of change in differential capacitance for different sensor configurations, in accordance with the present technology. On the vertical axis is the change in capacitance ($\Delta C$) in Ff. On the horizontal axis is the distance in mm.

The $\Delta C$ of differential measurement using PF, PR, and PH sensors is plotted. 5 mm is set as 0 fF for differential sensing. When the differential measurement was applied on $\Delta C$, the sensitivity was further increased with better linearity. The larger sensitivity and the better linearity came from the cancellation of the nonlinear terms for proximity response. PH electrodes showed the highest $\Delta C$ due to the reduced $C_0$ without an eyeball and the larger $C_1$ with an eyeball. The larger $\Delta C$ resulted in the enhanced sensitivity ($\Delta C/\Delta d$).

Figure 1I:
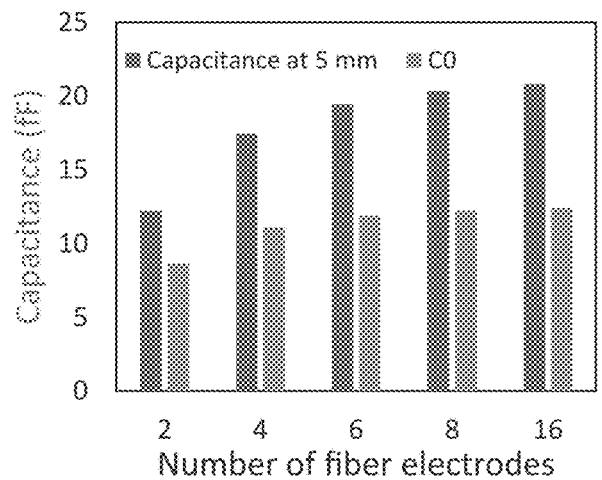
FIG. 1I is a graph of capacitance based on the number of fiber electrodes in an example sensor, in accordance with the present technology.

FIG. 1I is a graph of capacitance based on the number of fiber electrodes in an example sensor, in accordance with the present technology. On the vertical axis is the capacitance in fF. On the horizontal axis is the number of fiber electrodes. The initial capacitance ($C_0$) and the capacitance at 5 mm ($C_1$) of a PH sensor depending on the number of fibers in the fibrous electrode of the paired sensor. Capacitance for the spherical target at 5 mm and the capacitance without target ($C_0$). The $C_0$, $C_1$, and $\Delta C$ saturated as the number of fibers increased for a hybrid capacitance.

When the number of fibers increased from 2 to 16, $\Delta C$ saturated when the number was greater than 8. Despite the random fiber shapes, the aspect ratio (length/width) greater 100 and the fiber number greater than 8 could potentially offer uniform $\Delta C$ values due to the saturation. According to the numerical study, PH electrodes showed higher sensitivity due to the reduced initial capacitance and increased capacitance with a charged eyeball. A differential measurement could then increase sensitivity for proximity detection. An array of high aspect ratio fibers could offer uniform $\Delta C$. In some embodiments, the first electrode of the horizontal sensor is a fibrous electrode. In some embodiments, the fibrous electrode has 8 or more fibers. Similarly, in some embodiments, the first electrode of the vertical sensor is a fibrous electrode. In some embodiments, the fibrous electrode has 8 or more fibers.

FIGS. 2A-2D show an example numerical model for three sensor configurations, in accordance with the present technology. A COMSOL numerical model was built to study the proximity sensitivity of a capacitive sensor.

Figure 2A:
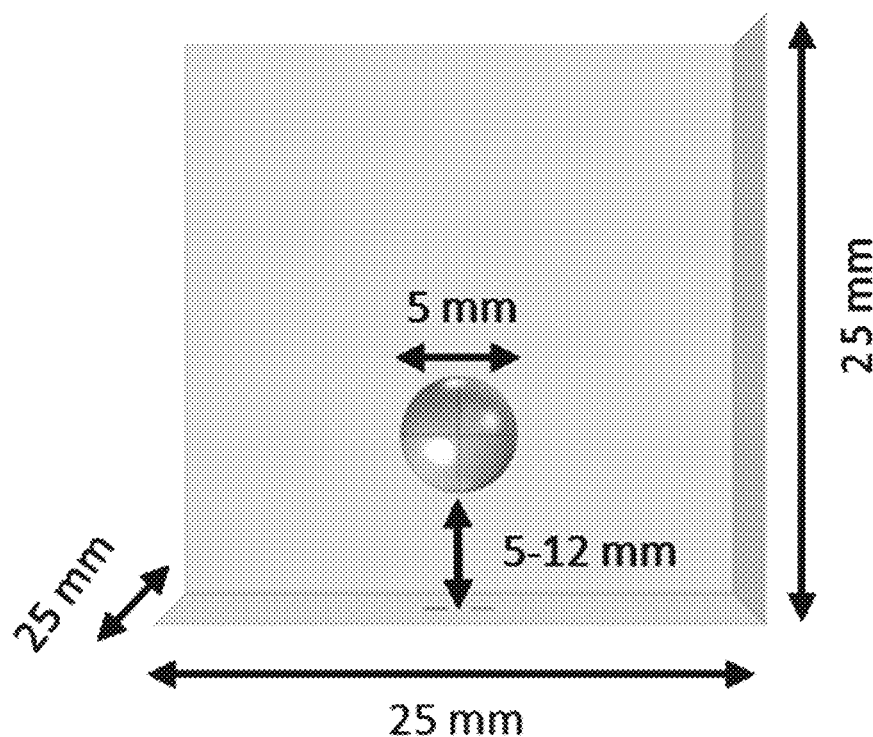
FIGS. 2A-2D show an example numerical model for three sensor configurations, in accordance with the present technology.
Figure 2B:
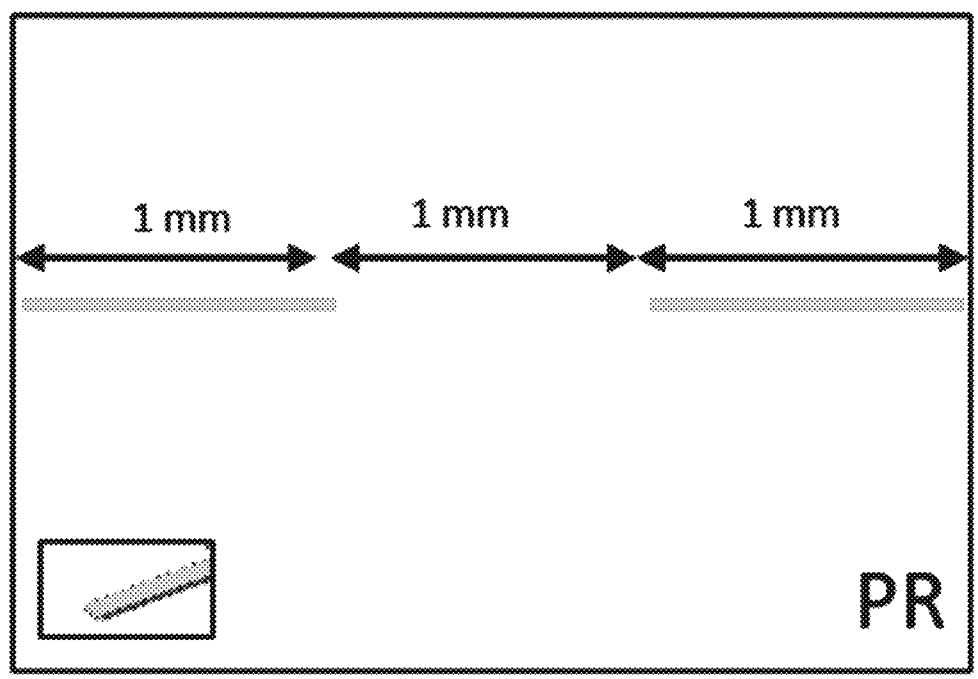
Figure 2C:
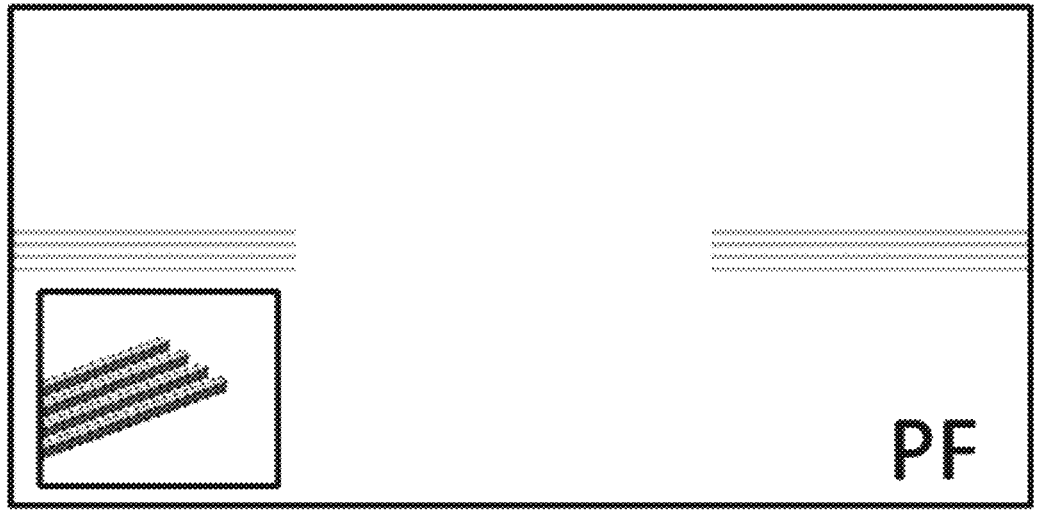
Figure 2D:
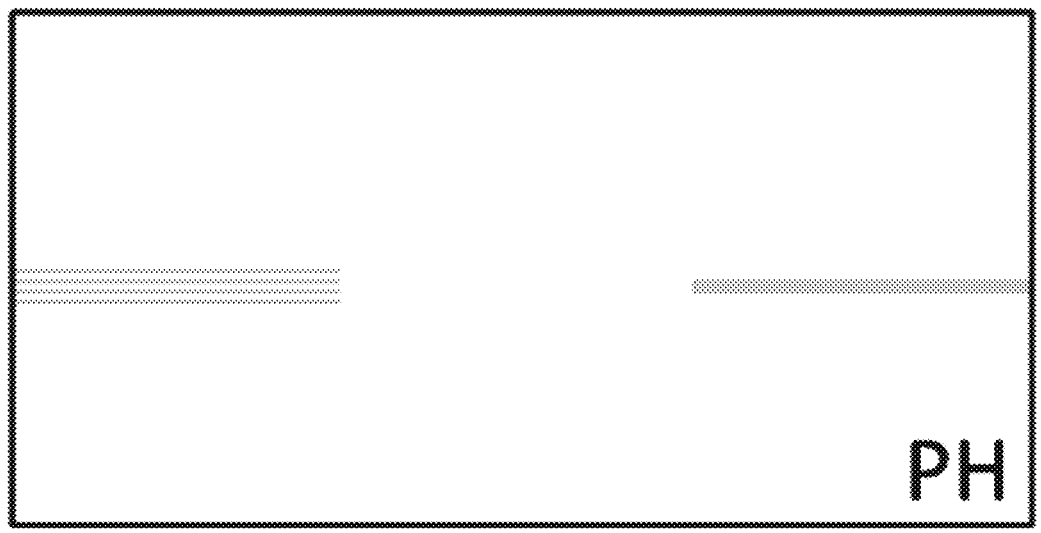

FIG. 2A shows the geometry of a spherical object mimicking an eyeball and paired electrodes for capacitive detection, in accordance with the present technology. Capacitive sensors were placed at the bottom of a square domain with air permittivity. One side was 25 mm. The potential of 5V was applied between two electrodes. The capacitive sensors were made of paired rectangular (PR), paired fibrous (PF), and paired hybrid (PH) electrodes (FIGS. 2B-2D). Three different types of geometries were compared to study a capacitive sensitivity to proximity detection of a charged object. For all the electrodes, the total volume was designed to be the same. The rectangular electrode was represented by a monolithic rectangular slab with has a cross-section of 40×10 µm2 with 1 mm in length. The geometry of the fibrous electrode was created by placing four parallel rectangular fibers at 20 µm apart. In some embodiments, each electrode has 10×10 µm2 in cross-section and is 1 mm in length. For hybrid electrodes, 5V was applied to the fibrous electrode while the rectangular electrode was grounded. A 25 kHz frequency was applied for an electrostatic model. The sphere had a dielectric constant of 80. For all configurations, the gap size was 1 mm, but the gap size between the electrodes may range from 0.1 µm to 1 mm. The 5 mm-diameter target represented a capacitive sensing target floating in the center. The observed capacitance was calculated from the imaginary part of the admittance, which is:

$$C = \frac{imag(Y_{11})}{\omega}$$

The symbol Y is the observed admittance at an electrode, and the ω is the excitation radian frequency, which is 50,000 πrad/s. A numerical model was built for the three sensor configurations with an eyeball. The rectangular metal electrode was 40×10 µm$^2$ in cross-section and 1 mm in length. The fibrous electrode was composed of four fibers having 10×10 µm$^2$ in cross-section and 1 mm in length. According to the numerical results, as the distance of the sphere to the sensor decreased from 6 to 4 mm, the charge interaction increased significantly between the eyeball and the positive electrode (as shown in FIG. 1D). In other words, the charge from the eyeball could increase the capacitance change (ΔC).

Figure 3:
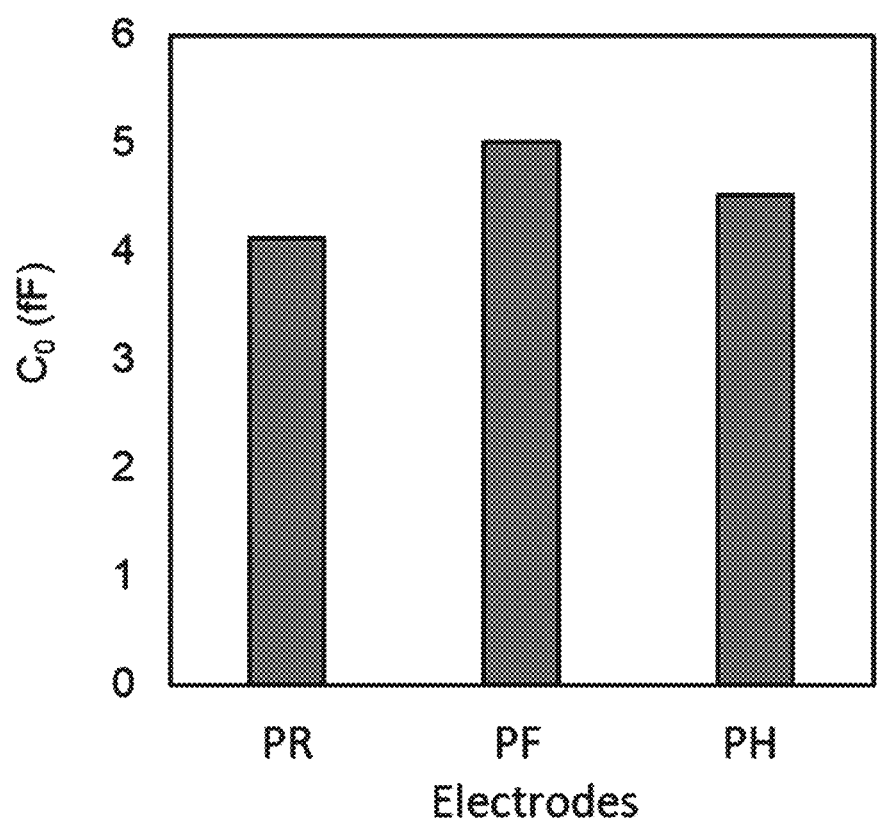
FIG. 3 is an initial capacitance measurement, in accordance with the present technology.

FIG. 3 is a graph of an initial capacitance measurement, in accordance with the present technology. On the vertical axis is the initial capacitance ($C_0$) in fF. On the horizontal axis are the three configurations of electrodes (PR, PF, and PH).

Without the eyeball, the initial capacitance of PR, PH, and PF sensors increased sequentially due to the increased surface area. When the eyeball was moved between 4 and 6 mm with an interval of 0.5 mm, the ΔC increased continuously.

FIG. 4A is an example of sensor fabrication, in accordance with the present technology. A capacitive sensor was made of carbon nanotube-cellulose fiber composites (CPC). The fabricated CPC had a mean thickness of 88.4±3.1 µm. For sensor fabrication, the material was cut into 1×10 mm$^2$. After patterning silver electrodes on both ends (MG Chemicals, 8330S-21G, USA), a water line was printed to induce cracking location followed by tensional fracture. Through the process, a fibrous electrode was fabricated. For rectangular electrodes, silver ink (Engineered Materials Systems, Inc. Cl-1001, NY) was uniformly coated on a polyethylene terephthalate (PET) film. A silver-coated PET film was trimmed to 1×5 mm$^2$. By combining fibrous and rectangular electrodes, three kinds of electrode pairs were fabricated; PF, PH, and PR electrodes. A 50 µm-thick self-adhesive polyethylene terephthalate (PET) film was used for laminating the capacitive sensors.

FIG. 4B is an illustration of example sensor configurations, in accordance with the present technology. The fabricated PF, PH, and PR sensors are shown. The gap between electrodes was 1 mm.

FIG. 4C is an optical and SEM image of an example sensor, in accordance with the present technology. The capacitive sensor was fabricated by fracturing a carbon nanotube (CNT)-paper composite. The composite was stretched to induce a crack in the CPC. The fractured composite was infiltrated with the polymer (polyurethane) for the structural integrity of the sensor. The crack creates a gap of 300~500 µm between the two CPC sides that are composed of 10 nm diameter MWCNTs with 10~100 µm in length. According to scanning electron microscope (SEM) study, the average thickness of fibers was 5.9±1.6 µm. The aspect ratio determining the electric field strength ranged from 200 to 490. The linear density of fibers was 14.5±3.6 mm$^{-1}$.

Figure 4D:
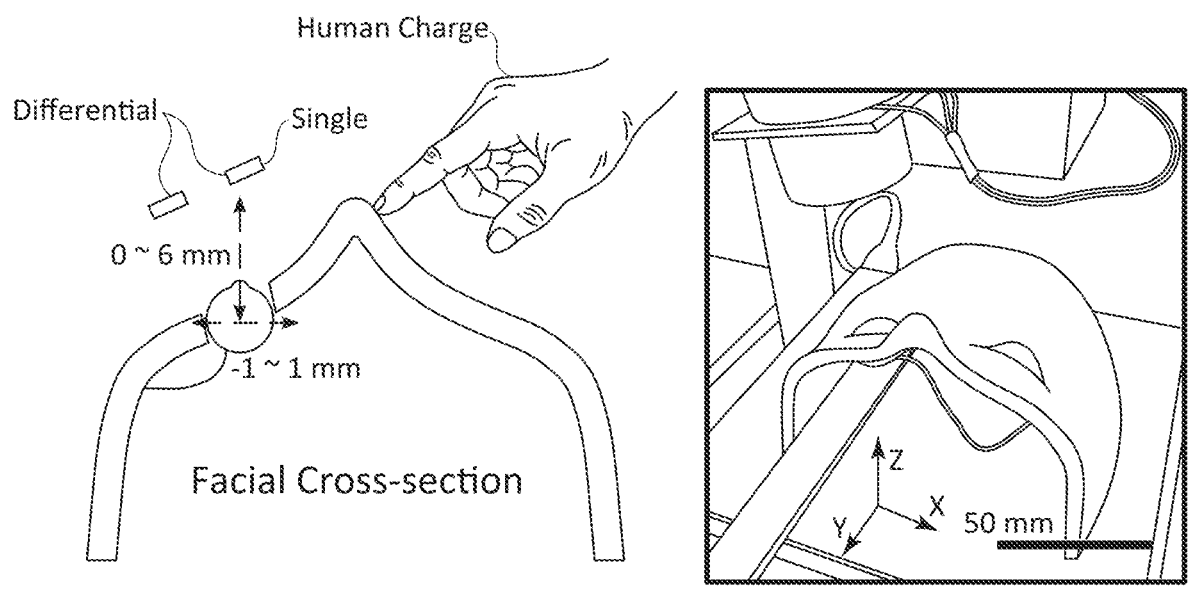
FIG. 4D is an eye and face simulator covered with a conductive aluminum foil for testing, in accordance with the present technology.

FIG. 4D is an eye and face simulator covered with a conductive aluminum foil for testing, in accordance with the present technology. An eye and a face simulator covered with a conductive aluminum foil was constructed. The response of the fabricated capacitive sensors was characterized by using a face simulator to study ΔC according to the sensor configurations, the geometry, and electric charge of a human face model with an eyeball. The human face model corresponding to an eyeball was 3D-printed using a polylactic acid (PLA). The face and eyeball were covered with conductive aluminum foil and connected via a copper wire. The eyeball was placed on a manual x-y-z stage to simulate human eye movement. The facial model and eyeball were located on an x-y plane, with stepper motor control along the z-axis. The body charge was applied to the facial model via a copper wire attached to the hand of a human subject. Capacitive sensors were placed at the bottom of a 3D printed PLA puck, which was titled at 10 degrees to match the contour of the facial model and directed towards the eyeball. Sensors were connected to a capacitance-to-digital chip and a microprocessor.

Figure 4E:
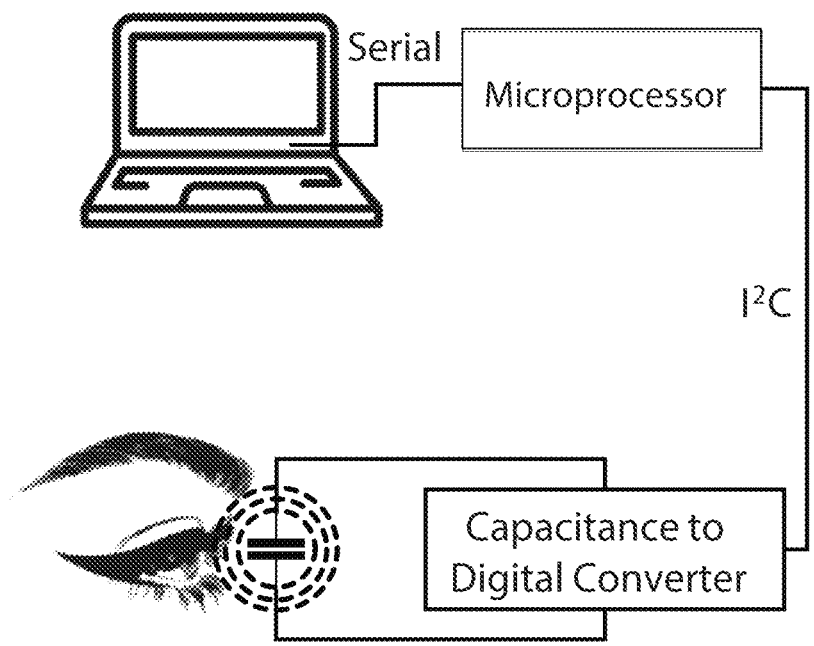
FIG. 4E shows an example capacitive measurement configuration, in accordance with the present technology.

FIG. 4E is shows an example capacitive measurement configuration, in accordance with the present technology. The capacitance measurement configuration using a capacitance-to-digital chip is illustrated. The face model (as shown in FIG. 4D) has the geometry of a human face with an independent actuation of the eyeball and the nearby sensor. A human charge was mimicked by touching the aluminum-covered face model with the finger to transfer human charge to the conductive surface. FIG. 4E shows the electric measurement configuration. A capacitance-to-digital chip (Analog Devices, AD7747) was interfaced to an Atmega microprocessor through I$^2$C interface. The digitized capacitance data were collected by a laptop computer. For capacitive detection, the non-spherical geometrical shape of the eye near the scleral-corneal junction changed the distance between a sensor and an eye. The change affected the fringing field, which subsequently changed the capacitance. This ΔC could be measured by either single- or differential capacitive sensors. Two kinds of capacitance-to-digital converters (CDC) were used to measure capacitance, AD7747 (Analog Devices) and FDC1004 (Texas Instruments). An AD7747 chipset was used for single- or differential measurement of capacitance. An AD7747 chip was powered by a 3.3 V input, enabling a 16 kHz excitation output and 45 Hz sampling rate. Although an AD7747 offered a high accuracy capacitance measurement (0.1 aF), the chip could measure only two capacitance values.

Using the setup, three tests were conducted to characterize the sensitivity of the capacitive sensors against various facial conditions. In Test 1, PR, PF, and PH sensors were displaced by 6 mm from the face fixed with an eyeball to characterize the sensitivity depending on the facial shape and body charge. Test 2 was to evaluate the most sensitive PH sensor only when the eyeball was displaced 0 to 6 mm from the face. This test could also provide $\Delta C$ depending on the charge induced by the eyeball. Test 3 was to compare single sensor configuration to differential sensors for ±1 mm-horizontal eye movement at 6 mm-distance. This test aimed to emulate a portion of actual eyeball movement during smooth pursuit. Tests 2 and 3 were performed with 1 mm-wide PH sensors, with and without body charge.

For human eye tests, the most sensitive PH sensor was used. A vertical eye movement test protocol was devised to evaluate sensor performance, whereby a human subject gazed at markers to rotate the eye vertically ±20°. To calibrate vertical eye movements, a whiteboard was placed 680 mm away from the user's eyes and marked with two points, 248 mm above and below the neutral gaze position. Moving the gaze between these two markers was equal to a vertical angular rotation of ±20°. Eye gazing was restricted to vertical movement, negating any diagonal or circular pathways. To ensure uniformity between tests, an eye movement protocol was designed to direct the human subject's gaze between markers. The eye movement process for vertical tests was as follows; Three repetitions of vertical movement between the ±20° markers, three repetitions of upward 0~20° from neutral location, and two repetitions of downward 0~20° from neutral position. An alarm timer indicated the time to move between two positions and the duration to hold the gaze at a marker. Movement time between markers was 1 s, with a hold time of 3 s at each marker. The eye displacement test was used to characterize the sensors, with respect to position, $\Delta C$, and sensitivity.

For horizontal eye movement, differential capacitive measurement was conducted to study the optimal sensor locations. The same experimental setup was used but the gaze moved between two markers located ±35° from the central position. The subject made alternating left- and right 70° horizontal eye movements between the two markers. The amplitude of horizontal eye movements was limited by the individual oculomotor limit of the subjects. Single capacitive horizontal measurement was not conducted due to the low sensitivity.

The capacitive sensor signals of vertical and horizontal eye movements were compared to the eye tracking outputs of a commercial eye tracker (Tobii Pro Nano). The eye tracker was a screen-based eye tracker that captured gaze data at 60 Hz and was designed for fixation-based studies. The eye tracker used video-based pupil and corneal reflection eye tracking with dark and bright pupil illumination modes. One camera captured images of both eyes for accurate measurement of eye gaze and eye position in 3D space, as well as pupil diameter. The capacitive eye tracker's signal was compared to that of the commercial eye tracker.

The capacitive eye tracker was assembled with one pair of differential sensors for horizontal eye tracking, together with a single sensor for vertical eye movement detection using FDC1004. The sampling rate was 45 Hz for 15 s. The time-dependent capacitive data were horizontal and vertical movement for differential and single measurements, respectively. The test was conducted on three human subjects. Due to the comparison to a commercial eye tracker, vertical and horizontal angular displacements were ±9° and ±16°, respectively. The degree of angular displacement was determined by the monitor size (diagonal distance: 685 mm) of a commercial eye tracker and the distance from the monitor to the human subject's face (788 mm). The corresponding data for a commercial eye tracker were unity displacement for horizontal and vertical movement.

FIG. 4F is a graph showing the change in capacitance for different sensor configurations, in accordance with the present technology. The $\Delta C$ for hybrid, fibrous, and rectangular sensors for 0~6 mm displacement between a face plus eyeball and a sensor (N=3). $\Delta C$ is measured with and without human charge. The presence of the human facial shape and charge profoundly affected the $\Delta C$ of the capacitive sensors. FIG. 4F compares $\Delta C$ of PH, PF, and PR sensors for the 0~6 mm-displacement between the sensors and the face with an eyeball with and without human charge. The starting position of 0 mm did not include a 50 μm-thick PET film thickness that covered sensors. In the comparison, the PH sensors showed the largest $\Delta C$ of 0.224 pF and 0.200 pF with and without a human charge, respectively. A PF sensor showed a $\Delta C$ of 0.175 pF and 0.160 pF with and without a human charge, respectively. The PR sensor showed the smallest $\Delta C$. These experimental data qualitatively agreed with the results of the numerical analysis.

FIG. 4G is a graph showing the change in capacitance for different sensor configurations without moving a face, in accordance with the present technology. On the vertical axis is the change in capacitance in pF. On the horizontal axis is whether or not there was a charge between the paired hybrid (PH) electrodes. The $\Delta C$ for a hybrid sensor with the displacement of an eyeball without moving a face ($\Delta C$ for 0~6 mm distance) is shown.

The sensor is initially located at 0 mm from the sensor. A PH sensor showed only $\Delta C$=42 fF with the human charge. In comparison to the experiment moving a PH sensor from the entire face (FIG. 4F), $\Delta C$ was only 18.7%. Although the human charge contributed to increasing $\Delta C$, the isolated eye movement in comparison to the whole face movement showed only limited $\Delta C$. Considering the 6 mm-displacement, the actual capacitance change for human eye movement could be further reduced.

FIG. 4H is a comparison for the change of capacitance for single and differential capacitive measurement, in accordance with the present technology. On the vertical axis is the change in capacitance in pF. On the horizontal axis is the horizontal distance in millimeters. The comparison of $\Delta C$ for single- and differential capacitive measurement for ±1 mm horizontal movement of an eyeball at the distance of 6 mm to a sensor is shown. Besides the out-of-plane displacement, a human eye could move horizontally from a sensor.

When a single capacitive measurement was conducted for 1 mm-horizontal movement at 6 mm proximity of a sensor, the $\Delta C$ was only 1.7 fF, approaching the noise level of 0.5 $fF_{RMS}$. The differential capacitive measurement increased $\Delta C$ by 55%. Therefore, differential capacitive measurement increased $\Delta C$ and, thus, sensitivity.

Figure 5:
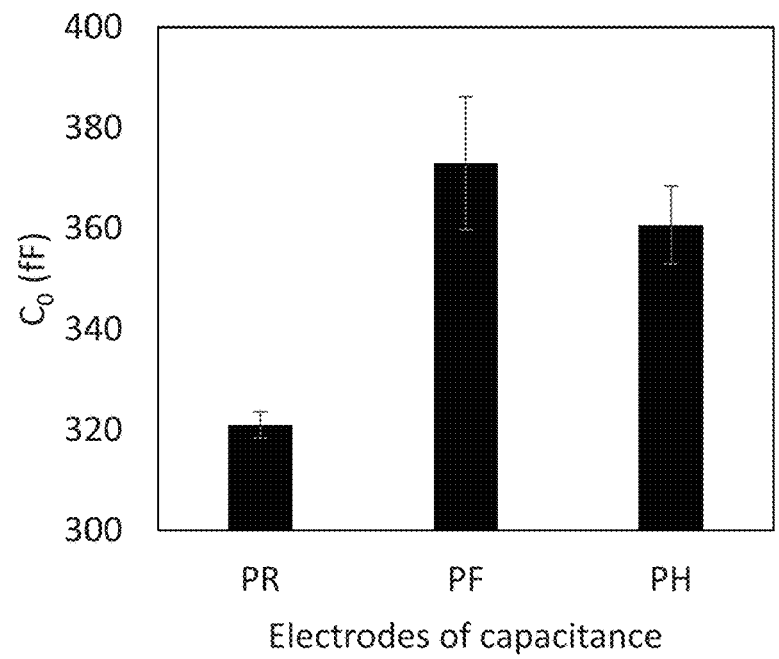
FIG. 5 is a graph of initial capacitance values for PR, PF, and PH electrodes, in accordance with the present technology.

FIG. 5 is a graph of initial capacitance values for PR, PF, and PH electrodes, in accordance with the present technology. On the vertical axis is the initial capacitance in fF. On the horizontal axis is the three configurations of electrodes (PR, PF, and PH) as described herein.

When $C_0$ values were compared for PR, PF, and PH electrodes, the average values were 321.0±2.6 fF, 373.0±13.2 fF, and 360.7±7.7 fF, respectively. The ratio of the standard deviation to the average was 0.8, 3.5, and 2.1% for PR, PF, and PH electrodes, respectively. The sequential increase of $C_0$ values for PR, PH, and PF electrodes agreed with the sequence of the numerical results (See FIG. 3).

Figure 6:
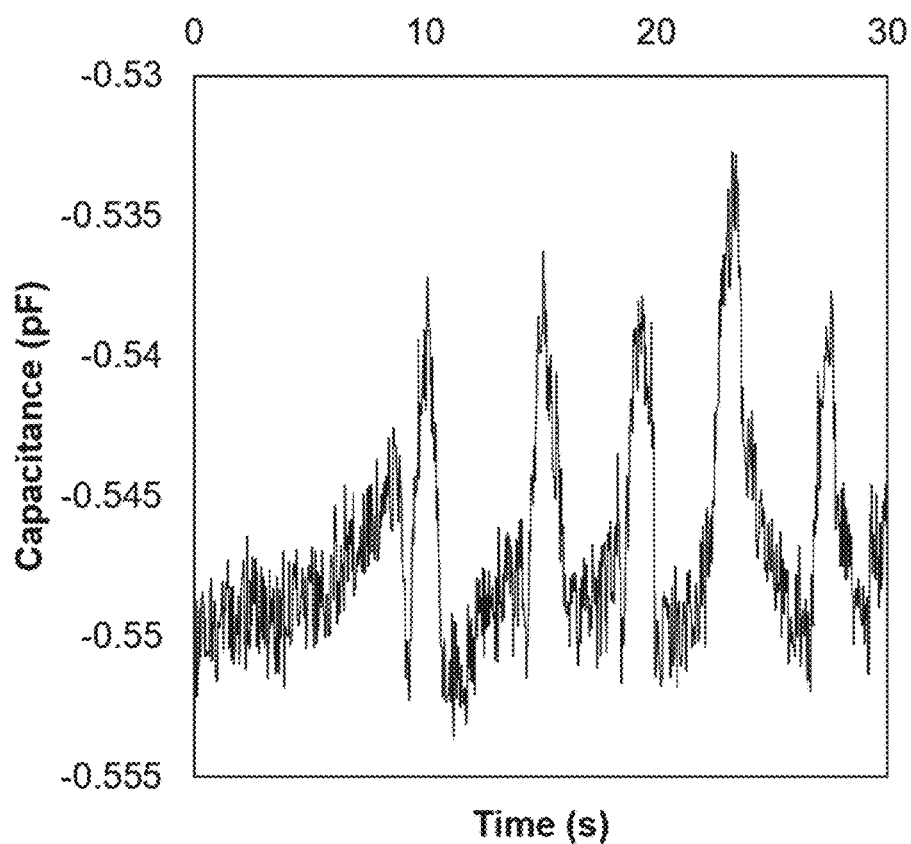
FIG. 6 is a graph of differential vertical sensors tracking left-right movements, in accordance with the present technology.

FIG. 6 is a graph of differential vertical sensors tracking left-right movements, in accordance with the present technology. On the vertical axis is the capacitance in pF. On the horizontal axis is the time in seconds. The label along the top of the graph is the time in seconds (0, 10, 20, and 30 s). For vertical eye movement, only a single measurement was conducted because differential capacitive measurement showed undesirable patterns.

Figure 7A:
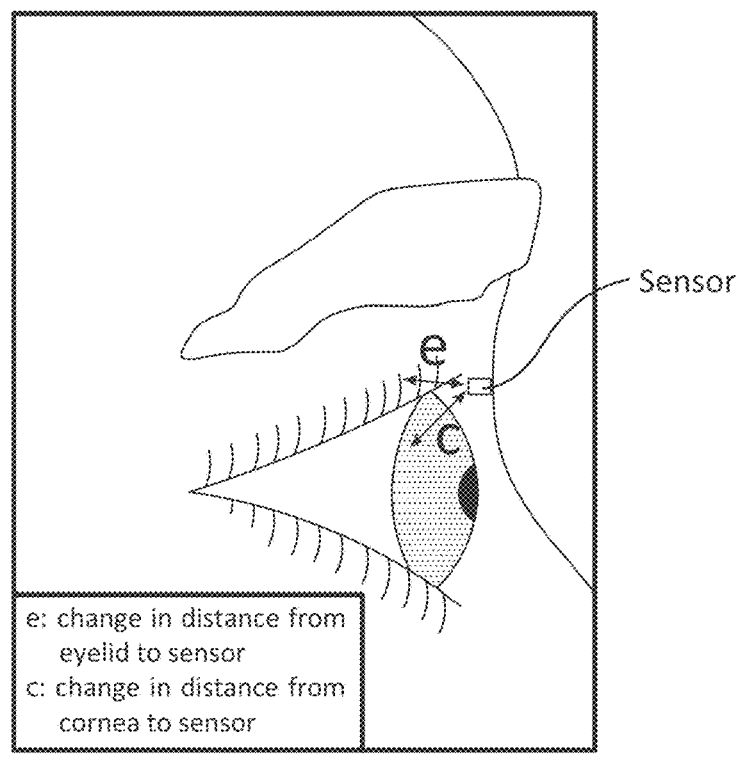
FIG. 7A is an image frame of one or 30 images taken during vertical smooth pursuit, in accordance with the present technology.

FIG. 7A is an illustrated image frame of one of 30 images taken during vertical smooth pursuit, in accordance with the present technology. The distance "e" is the change in distance from the eyelid to the sensor, whereas the distance "c" is the change in distance from the cornea to the sensor. It was speculated that the capacitive signal for vertical eye movement was dominated by cornea movement rather than eyelid movement. To evaluate the source of the capacitive signal, photographic angular analysis of the eye was conducted.

Figure 7B:
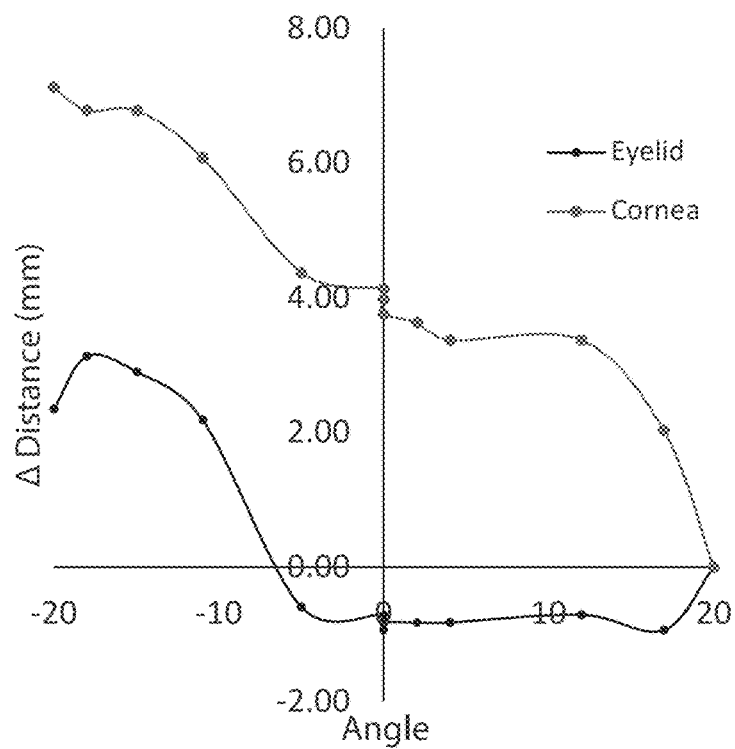
FIG. 7B is a graph of the distance change between a sensor and an eyelid, in accordance with the present technology.

FIG. 7B is a graph of the distance change between a sensor and an eyelid, in accordance with the present technology. On the vertical axis is distance in millimeters. On the horizontal axis is the vertical rotation angle.

A frame-by-frame photo was taken (as represented in FIG. 7A) to determine the displacement of the cornea and eyelid during vertical eye movement, with respect to sensor position. From the initial distance of 6 mm, the cornea was diagonally retracted by 7.1 mm from the vertical sensor position as the eye gazed between 20 to −20°. In comparison, the eyelid was located at −1 mm at 20° and withdrawn by 3 mm at −20°. This data confirmed a complex movement relationship between the cornea and eyelid, where the photographic displacement could not individually explain the relationship between the capacitance signal and gaze position.

Figure 7C:
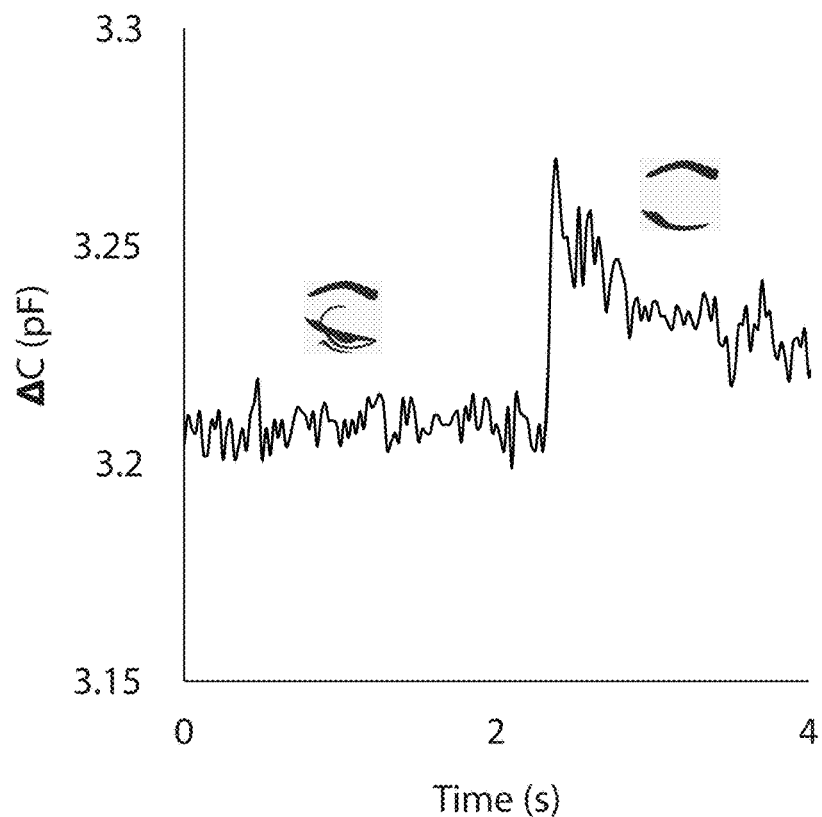
FIG. 7C is a graph showing the capacitance change from a nearly closed eye to a fully closed eye, in accordance with the present technology.

FIG. 7C is a graph showing the capacitance change from a nearly closed eye to a fully closed eye, in accordance with the present technology. As such, the capacitance effect of the eyelid encasing the cornea was also examined. On the vertical axis is the change in capacitance in pF. On the horizontal axis is the time in seconds. As the eyelid moved from nearly closed to a fully closed state, a sharp spike rose in capacitance. The dielectric nature and electric charge of the cornea and eyelid could impact the dominancy of $\Delta C$.

Figure 7D:
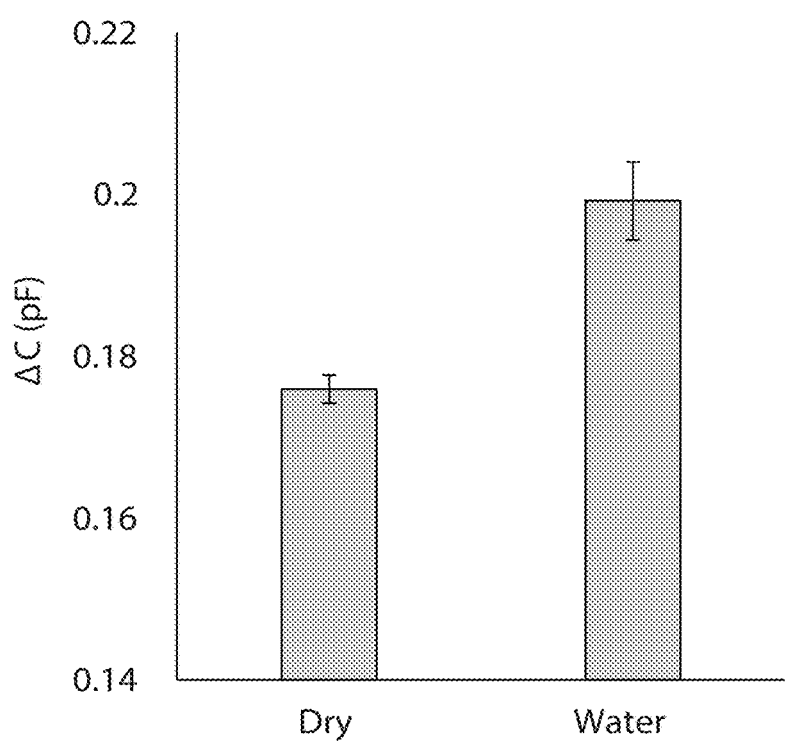
FIG. 7D is a graph showing the capacitance change between dry and wet skin, in accordance with the present technology.

FIG. 7D is a graph showing the capacitance change between dry and wet skin, in accordance with the present technology. On the vertical axis is the change in capacitance. On the horizontal axis is dry skin and skin wet with water. To mimic the capacitance interaction between a wet eyeball and dry eyelid, when a sensor moved between wet and dry skin, the capacitance change was much greater on the wet skin. On average, the wet skin exhibited $\Delta C$ of 24 fF, greater than that of the dry skin. The larger $\Delta C$ could be caused by direct electrical connection to the human body charge and the electrical double layer forming on the skin.

Figure 8A:
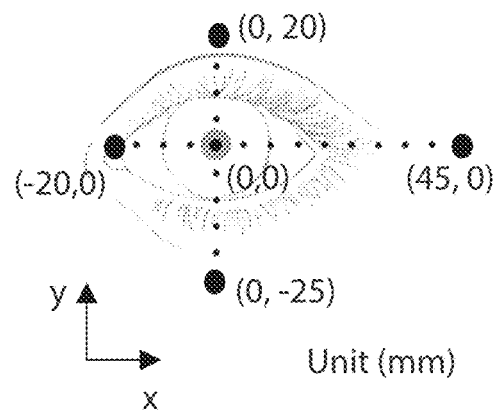
FIG. 8A is example locations for sensors for single and differential capacitive measurement, in accordance with the present technology.
Figure 8B:
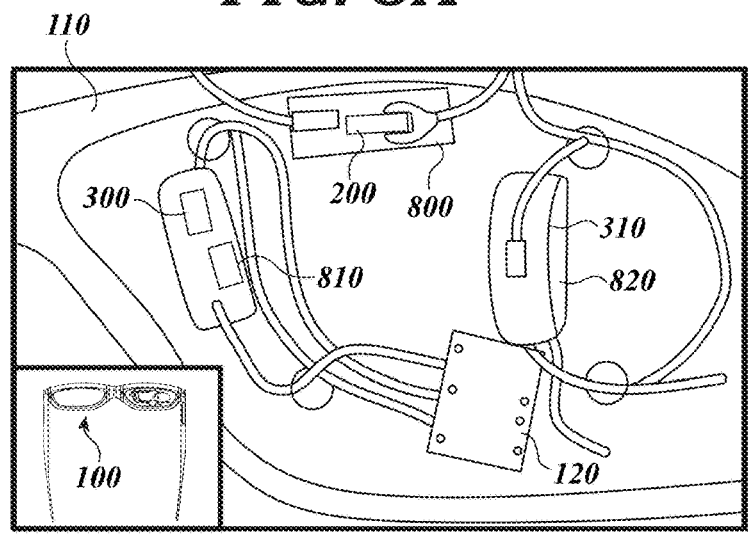
FIG. 8B is example monocular eyeglasses with single vertical and differential horizontal sensors, in accordance with the present technology.
Figure 8B:
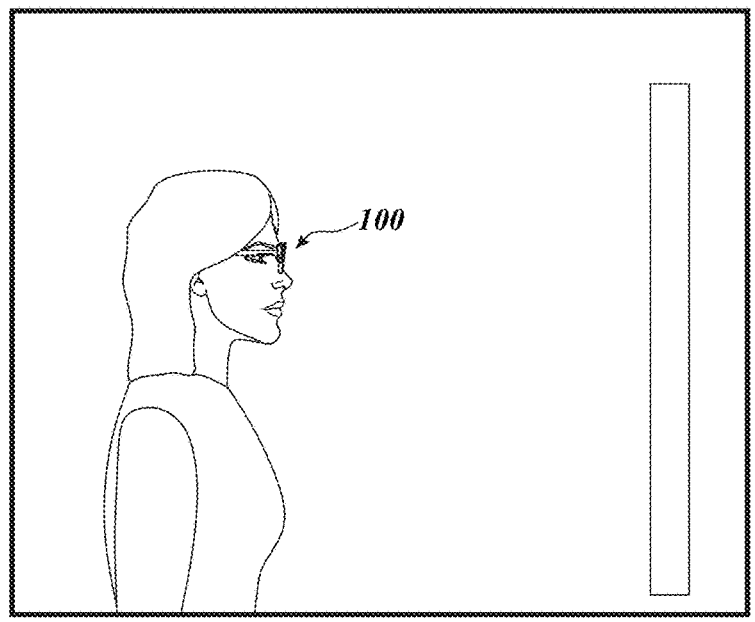

FIG. 8A is example locations for sensors for single and differential capacitive measurement, in accordance with the present technology. The corner of the figure shows an x, y plane used to demonstrate the location, with the locations plotted on a coordinate system. The capacitance change due to the fringing electric field could be measured by either singled-ended (FIG. 8A, left side) or differential methods (FIG. 8A, right side). The single-ended method was convenient but suffered from the nonlinear relationship between capacitance and the distance to the object. The differential method applied an $\Delta C$ voltage 180° out of phase to the second sensor. The differential method canceled the nonlinearity and increased the sensitivity.

FIG. 8B shows example monocular eyeglasses with single vertical and differential horizontal sensors, in accordance with the present technology. For differential measurement, four sensors were installed on a pair of glasses. The asymmetry in the geometrical shape of the eye near the scleral-corneal junction caused the eye's distance to the sensor to change as it rotated. The distance change affected the fringing electric field, which in turn changed the capacitance.

The top image in FIG. 8B shows a zoomed in image of the eye tracking system 100. As shown in the image, in some embodiments, the eye-tracking system 100 comprises an article 110, at least one vertical sensor 200, at least one horizontal sensor 300 and a second horizontal sensor 310. In some embodiments, the eye-tracking system 100 includes an processor 120, which may include an electronic control unit. In some embodiments, the processor 120 is not attached to the article 110 and is communicatively coupled to the at least one vertical sensor 200, the at least one horizontal sensor 300, and the second horizontal sensor 310. In some embodiments, the electronic control unit/processor 120 is connected to the sensors 200, 300, 310 through a wired connection, but in some embodiments, the electronic control unit/processor 120 is connected to the sensors 200, 300, 310 through a wireless connection, such as Bluetooth.

In some embodiments, the eye-tracker 100 further includes spacers, 800, 810, 820 to lift the sensors 200, 300, 310 from the article 110 and bring them into closer proximity with a user.

An FDC1004 chip was used to construct the eye tracker circuitry for benchmarking against the Tobii Pro Nano. FDC1004 was powered by a 3.3 V input. The excitation frequency was 25 kHz with a measurement resolution of 0.5 fF. PDC1004 was capable of four single or two pairs of differential sensors, with a sampling rate of up to 100 Hz/sensor. The multiplexing capability to accommodate four capacitive sensors allowed for simultaneous measurement of horizontal and vertical eye movement over 60 Hz that was a standard for camera-based eye trackers. In some embodiments, the sampling rate ranges from 10 Hz to 99 Hz. Note that the maximum sampling rate of 100 Hz could not be used due to the reduced accuracy.

In some embodiments, an eye tracking sensor including capacitive sensors including a template material including a plurality of electrodes to form a capacitance, wherein the plurality of electrodes detects the distance to an eyeball or eyelid in order to trace the movement of an eyeball is disclosed. In some embodiments, the sensor locations are designated for specific eye movement and rotation. A limited number of sensors may be used to reduce parasitic capacitance, simplify the configuration, and guarantee the optical transparency of eyeglasses.

In operation, the capacitive sensors are used with the combination of single-ended and differential setups. Depending on the locations, the sensitivity varies. The highest sensitivity of up-down motion is shown at the top of an eye (up/down) because cornea movement can be detected with distance change. The capacitance change may be amplified by the movement of eye lid. The sensor at the bottom is able to get the signal but with a lower amplitude. Differential configuration works for up/down, but single-ended configuration is good enough for up/down movement, as shown in FIG. 1A.

For left-right movement, a differential sensor configuration shows a better sensitivity. The sensitivity to left-right movement is limited because eye lid movement is not coupled with left/right movement. Single ended configuration showed less sensitivity. The capacitance signal is interfered with by body or face charge. The capacitance signal can be changed due to eye movement involving the change of electric charge. When the sensor is grounded to body, the capacitance signal change is enlarged. In some embodiments, the eye tracker includes an electronic ground configured to electrically connect the eye-tracking system to a body of the user in order to increase the capacitance change detected by the vertical and horizontal capacitive sensors. When the body is grounded and shared with the sensors, the circuit needs to be protected from electric shock. The adjustment of the angle or displacement of sensors improves the sensitivity due to the smaller distance and the greater facing area between a sensor and skin.

Signal drift is coupled with eye movement. Detrend (flattening) and low pass filters may be used to negate the noise and parasitic capacitance. Active and passive shielding may be used for the chip, wires, and sensors to improve the sensitivity, reduce the noise, and localize the electric field. A microprocessor, capacitance-digital chip, wireless or wired data transfer of the signal, data storage, and power units may be included.

A machine learning algorithm or artificial intelligence software may be incorporated to determine the eye movement. In some embodiments, the eye sensors can be applicable to diagnosis of neurological disorders, human-machine interface, sleep stage characterization, and sleep monitoring.

For vertical eye movement, a single capacitive measurement was conducted to study the optimal sensor location. In FIG. 8A, the locations of a sensor are presented. For vertical movement, the tested sensor 200 locations were tested from (0, 20) to (0, −25) by varying the vertical position in −5 mm increments. The origin of the coordinate represents the center point of the cornea. The x-y coordinates correspond to the x-y plane of the glasses shown in FIG. 1A. Vertical and horizontal eye movement was conducted according to the designed protocol by watching the spots on a whiteboard, as shown in the bottom image of FIG. 8B. While vertical movements were measured by single capacitance (at least one vertical sensor 200), horizontal differential sensors 300, 310 were also sensitive to the vertical movements. With the increased sensitivity of differential capacitance, the change in proximity of the cornea and eyelid to the differential sensors during vertical movement, led to detection of this movement as a sinusoidal pattern. As such, a single measurement was used to negate horizontal movement while enabling the sensitivity towards only vertical eye movements.

Figure 8C:
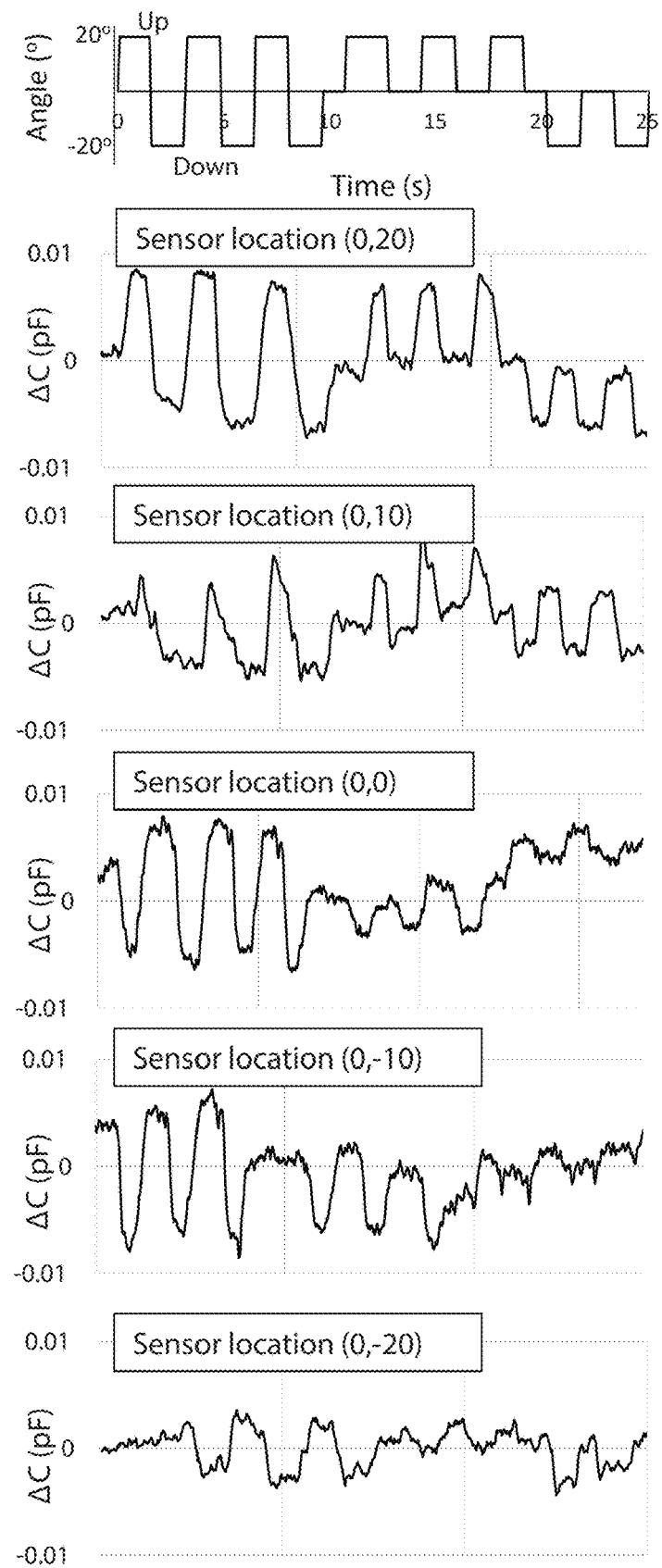
FIG. 8C is a change in capacitance depending on vertical sensor locations, in accordance with the present technology.

FIG. 8C shows a change in capacitance depending on vertical sensor locations, in accordance with the present technology. The ΔC depends on vertical sensor locations at (0, 20), (0, 10), (0, 0), (0, −10), and (0, −20). On the vertical axis of the first graph is the angle in degrees. On the vertical axis of each of the other graphs is the change in capacitance in pF. On the horizontal axis of all the graphs in FIG. 8C is the time in seconds.

The time-dependent protocol of eye movement in the top graph of FIG. 8C shows vertical displacement of ±20°. The sensor locations of (0, 20) to (0, 10) clearly show the reproducible measurement of eye movements and identified the straight neutral gaze at the midline. At the sensor location of (0, 0), the phase of ΔC was shifted because the sensor location was at close proximity to an eyeball. At the center location, the sensor failed to reproduce the vertical eye movements. As the sensor moved to (0, −10) and (0, −20), ΔC was inverted in comparison to that of (0, 20), as the sensors at these locations were inversely influenced by the eye. Moreover, the amplitude decreased as the sensor location was below (0, 0). In comparison to the downward movement, the amplitude of the upward movement was smaller due to the distance increase. This decrease in amplitude and signal inversion was further explained by the capacitive relationship between the cornea and eyelid to the sensors. At location (0, −25), the sensor produced inconsistent amplitude and severe distortion of the signal.

According to the results, the cornea with the thin water layer could dominate ΔC until the eyelid was completely closed. The inversion and decreased amplitude of ΔC at the vertical sensor locations (0,0) and below, could be explained with respect to cornea and eyelid protuberance. The signal was inverted at sensor locations (0,0) and below as the cornea was at a closer proximity to the sensor during its downward trajectory. The amplitude decreased, as less of the cornea was interacting with the sensor. In summary, the sensor location between (0, 20) and (0, 10) was optimal with a max amplitude of 20 fF and sensitivity of 0.5 fF/deg. The accuracy was 1.1 degrees.

Figure 8D:
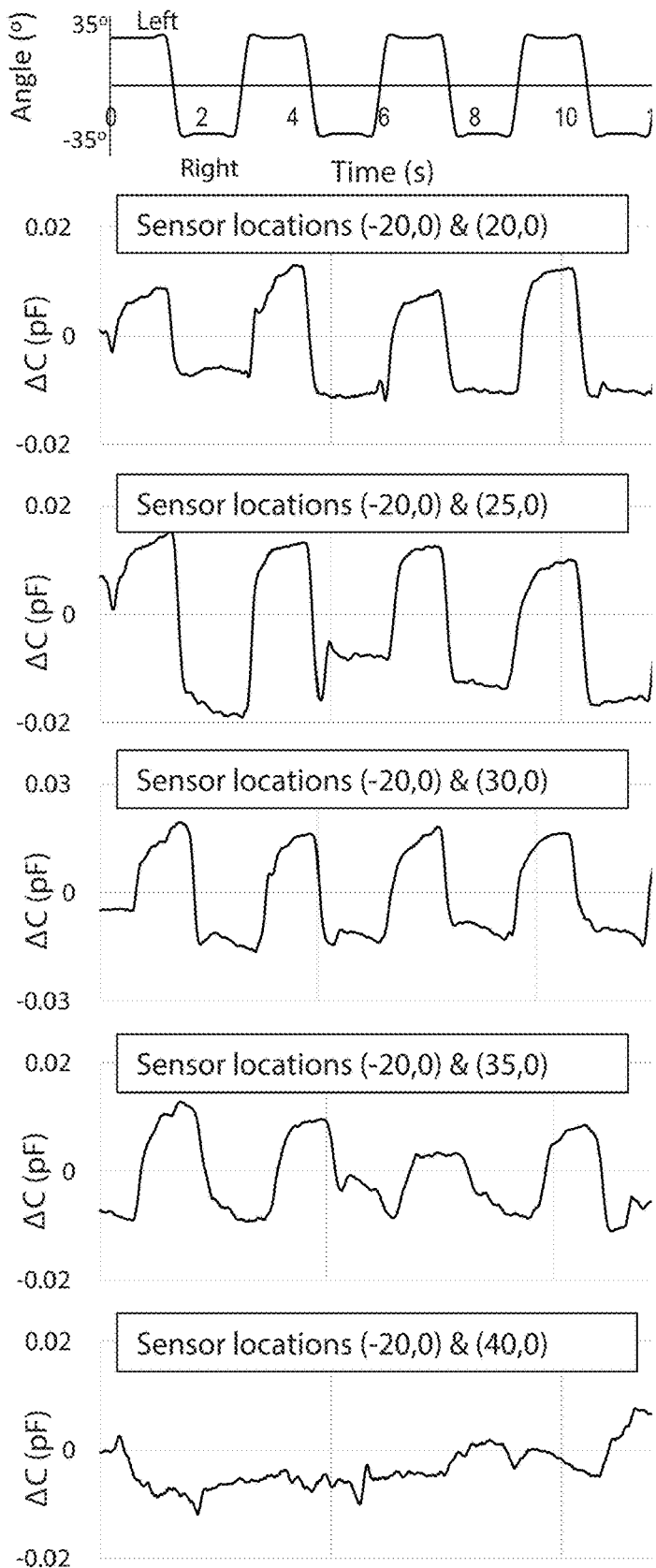
FIG. 8D is a change in capacitance depending on horizontal differential sensor locations, in accordance with the present technology.

FIG. 8D is a change in capacitance depending on horizontal differential sensor locations, in accordance with the present technology. On the vertical axis of the first graph is the angle in degrees. On the vertical axis of all other graphs is the change of capacitance in pF. On the horizontal axis of all the graphs is the time in seconds. The ΔC depending on horizontal differential sensor locations at [(−20, 0) and (20, 0)], [(−20, 0) and (25, 0)], [(−20, 0) and (30, 0)], [(−20, 0) and (35, 0)], and [(−20, 0) and (40, 0)] is shown.

For horizontal eye movement, differential capacitive measurement was chosen to study the optimal sensor locations. The same experimental protocol was used, but the gaze moved between two targets located at −35° (left) and +35° (right). The subjects repeated the 70° gaze shift five times for each direction. The horizontal eye movement excursion was limited by the subject's oculomotor range. Single capacitive measurement was not used due to the low sensitivity. Note that horizontal eye movement did not generate so measurable displacement as vertical movement.

Both sensors in the differential configuration were placed on the left and right sides of the right eye. The design of the glass frame only allowed the left sensor to be placed at (−20, 0) near the nose bridge. The location of the right-side sensor was tested between (20, 0) and (40, 0) in 5 mm increments to find an optimal location.

When the right sensor was located between (20, 0) and (30, 0), the capacitive signals clearly showed rightward, leftward, and zero-crossing movements. Moreover, the signals showed consistent movement amplitudes. At location (35, 0), the signal reduced amplitudes. At the most peripheral location (40, 0), the sensor failed to produce a predictable signal. The failure was caused by the lack of sensitivity from the right sensor because the sensor was located beyond the eye corner. Differential sensors located at [(−20, 0) & (20, 0)] and [(−20, 0) & (30, 0)] were optimal with a maximum amplitude of 30 fF and sensitivity of 0.43 fF/deg. With a noise level of 0.35 $fF_{RMS}$, the precision was within 0.82 degrees. The midline of the waveform corresponded to a straight neutral gaze.

The capacitive sensor signals of vertical and horizontal eye movements were compared with those produced by a camera-based commercial eye tracker (Tobii Pro Nano). The capacitive eye tracker was assembled with one pair of differential sensors for horizontal eye tracking, along with a single capacitive sensor for vertical detection. Subjects made both vertical and horizontal movements for the comparison study. Since the single- and differential sensors showed two time-dependent signals for eye tracking, the ΔC values of horizontal and vertical movements were compared with those of a commercial eye tracker.

Figure 9A:
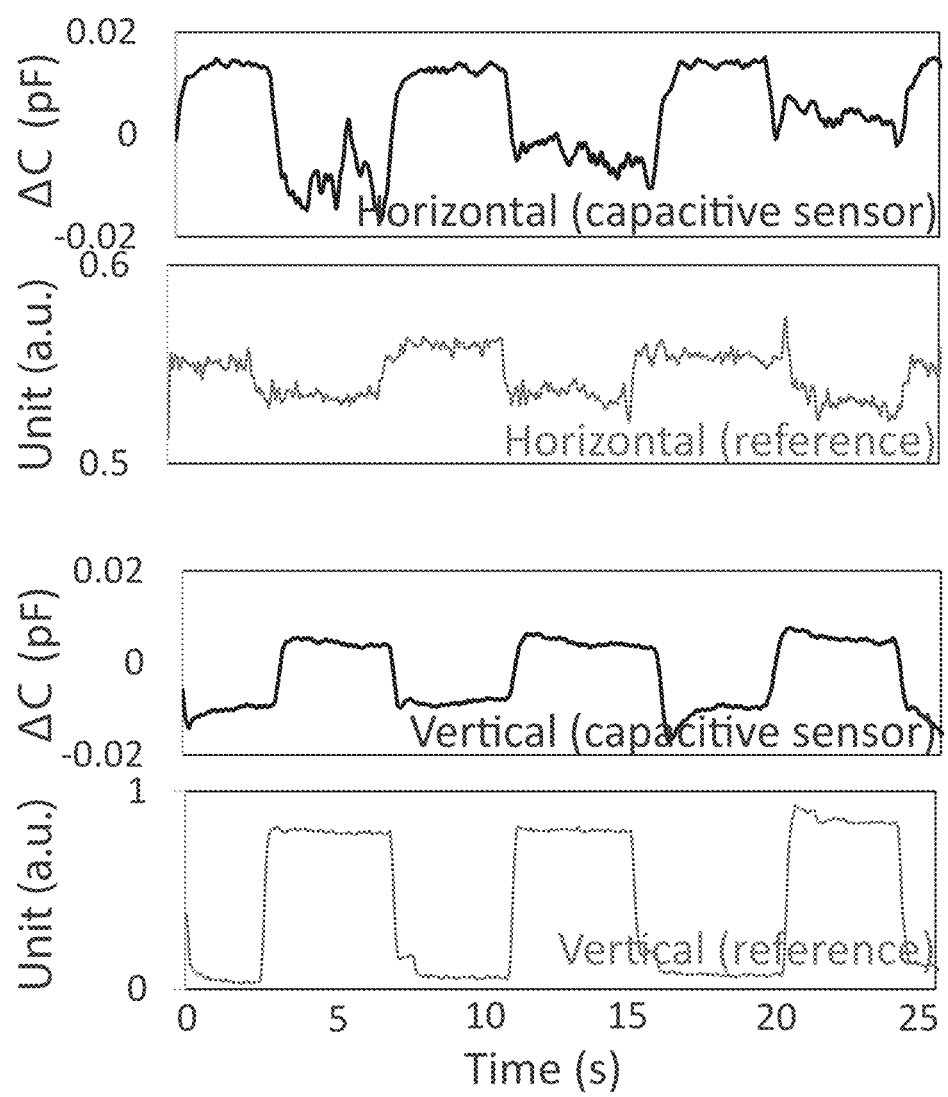
FIG. 9A shows the vertical movement of an eyeball, with a commercial eye-tracker and the disclosed eye tracker, in accordance with the present technology.

FIG. 9A shows the vertical movement of an eyeball, with a commercial eye-tracker and the disclosed eye tracker, in accordance with the present technology. The first graph shows the horizontal performance of the disclosed eye tracker, in comparison to the second graph, showing the horizontal performance of the commercial eye tracker. Similarly, the third graph shows the disclosed eye-tracker's vertical performance in comparison to the bottom graph, showing the commercial eye-tracker's vertical performance.

As the eye moved vertically, both the vertical and horizontal ΔC clearly showed the movement signals with similar amplitudes and opposite phases. The commercial eye tracker also produced eye movement signals in both the vertical and horizontal channels during a pure vertical eye movement, but the amplitude of the horizontal signal was ~3% of the vertical signal.

Figure 9B:
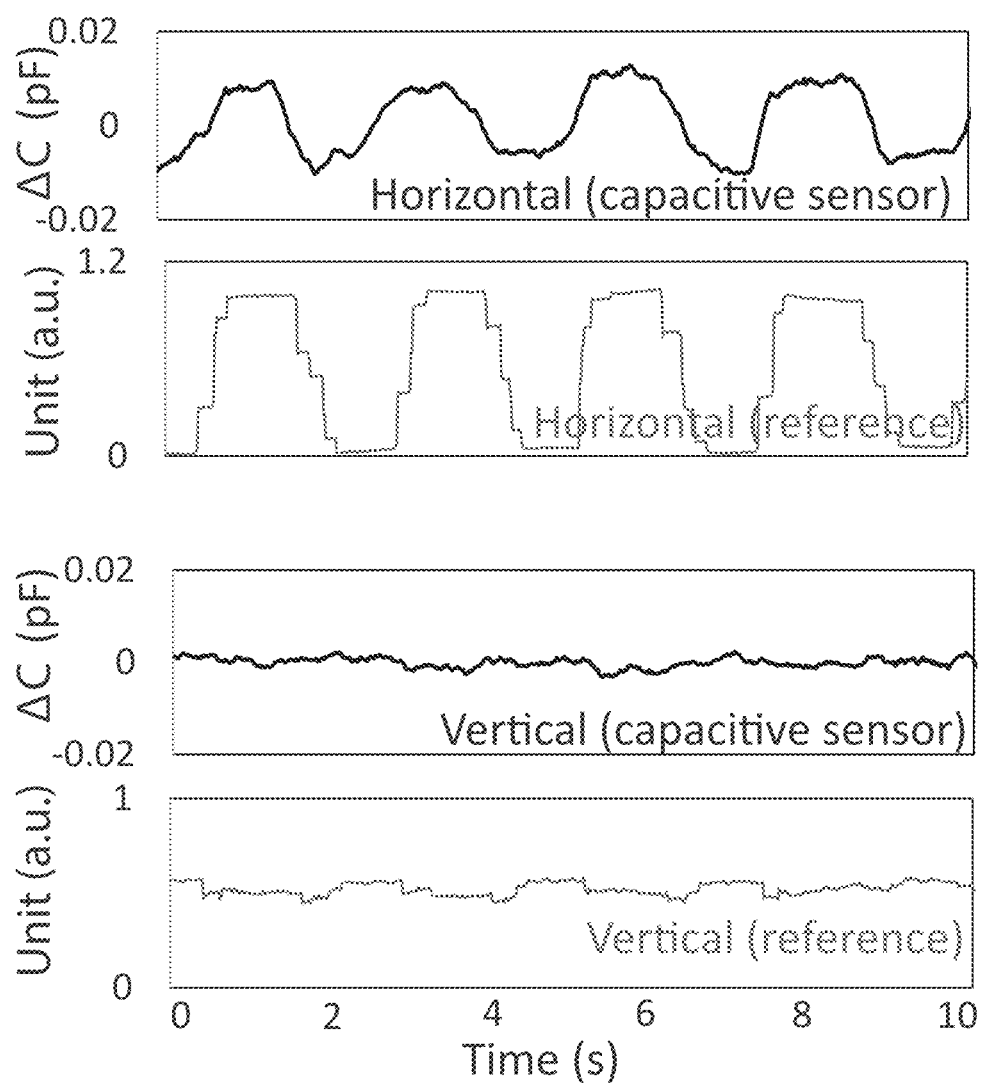
FIG. 9B shows the examples of horizontal eye movement signals with the disclosed eye tracker and a commercial eye tracker, in accordance with the present technology.

FIG. 9B shows the examples of horizontal eye movement signals with the disclosed eye tracker and a commercial eye tracker, in accordance with the present technology. FIG. 9B shows the comparisons of horizontal eye movement signals produced by the capacitive sensors (ΔC) and the Tobii eye tracker. In contrast to vertical eye movement, the horizontal ΔC showed a robust horizontal movement signal, but the vertical ΔC did not show any signals related to the horizontal eye movement. Based on the results, the vertical capacitive sensor determined the movement direction of an eyeball. The rotation angle of horizontal movement needed to be calibrated based on the amplitude of a vertical capacitive sensor. Based on the results shown in FIGS. 9A and 9B, combining both amplitude and phase information from both vertical and horizontal capacitive sensors allowed for horizontal and vertical signal separation due to the crosstalk during vertical eye movement.

Figure 9C:
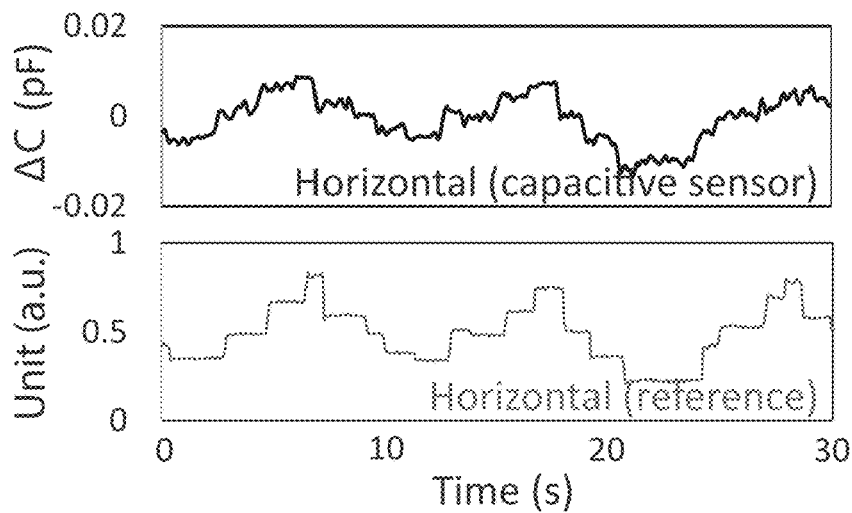
FIG. 9C shows horizontal eye movement signals with the disclosed eye tracker and the commercial eye-tracker, in accordance with the present technology.
Figure 9D:
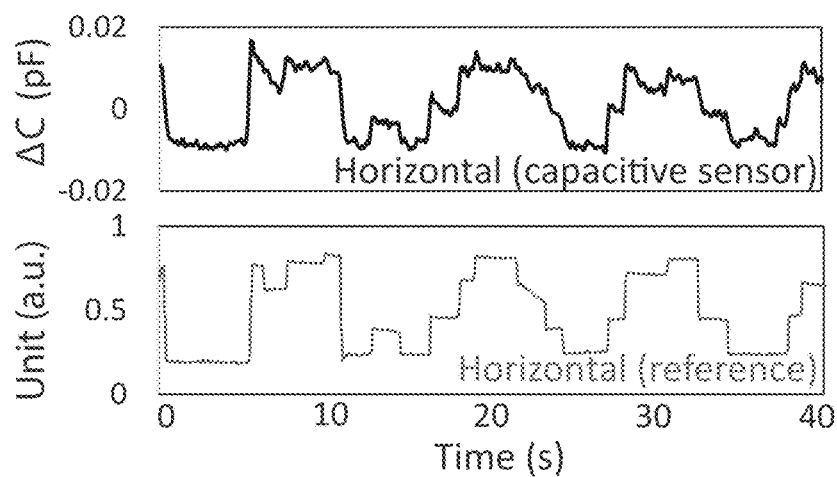
FIG. 9D shows horizontal eye movement signals with the disclosed eye-tracker and the commercial eye tracker, in accordance with the present technology.

FIG. 9C shows horizontal eye movement signals with the disclosed eye tracker and the commercial eye-tracker, in accordance with the present technology. FIG. 9D shows horizontal eye movement signals with the disclosed eye-tracker and the commercial eye tracker, in accordance with the present technology. The capacitive sensors clearly detected the saccades. In comparison to the ΔC shown in FIG. 9B (top panel), the saccadic eye movements were more distinctly shown and clearly correlated to those produced by a commercial eye tracker (bottom panel). Overall, ΔC ranged between 10~20 fF. Considering horizontal eye movements of ±12°, 1° accuracy could be achieved for horizontal eye movement.

Figure 9E:
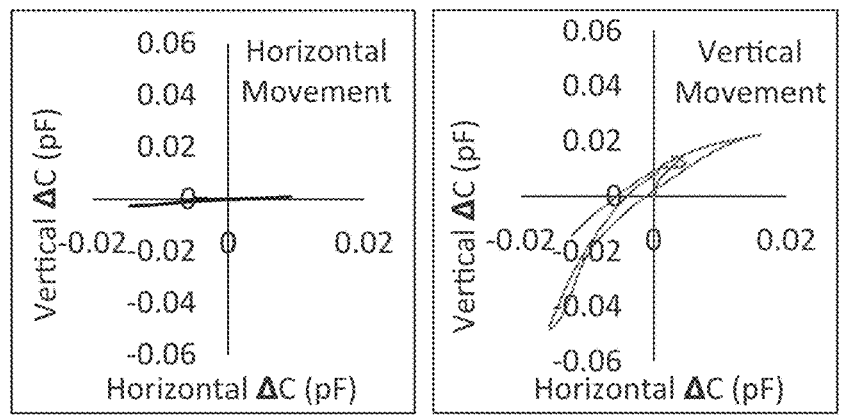
FIG. 9E depicts phase diagrams for vertical and horizontal smooth pursuit movement, in accordance with the present technology.

FIG. 9E depicts phase diagrams for vertical and horizontal smooth pursuit movement, in accordance with the present technology. The vertical and horizontal components from each of the smooth pursuit movements were plotted against each other to qualitatively deduce the direction of eye movement. During horizontal smooth pursuit the phase diagram produced a plot with negligible vertical amplitude. However, during vertical smooth pursuit, the phase diagram produced a plot with a diagonal characteristic, with horizontal and vertical amplitude. A clear qualitative distinction was evident between the phase diagrams, aiding in identifying between horizontal and vertical eye movement.

Figure 9F:
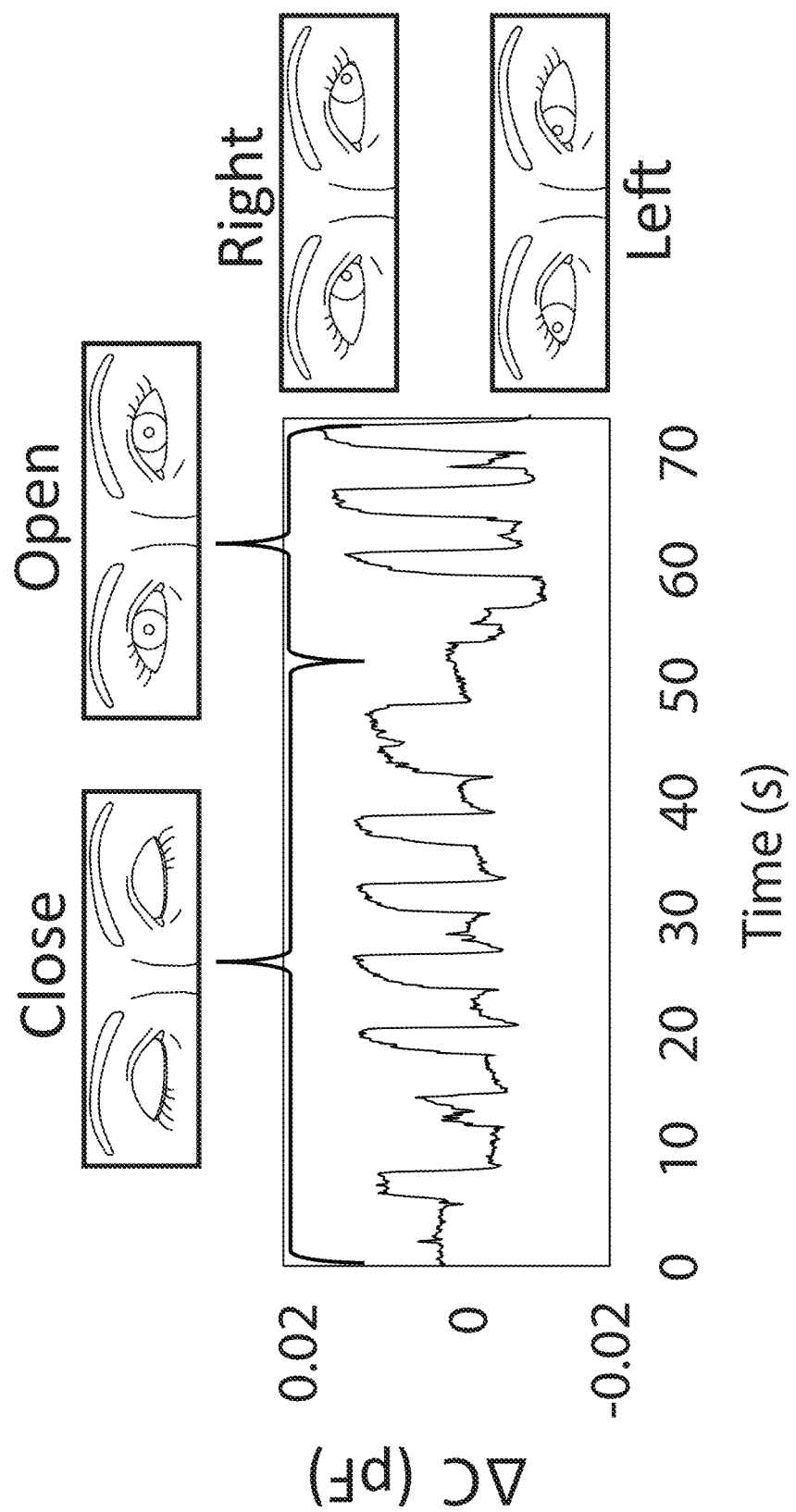
FIG. 9F shows horizontal eye movement with the eyelids closed and opened, in accordance with the present technology.

FIG. 9F shows horizontal eye movement with the eyelids closed and opened, in accordance with the present technology. The capacitive eye tracker was also tested to monitor horizontal eye movement with the eyelids closed and opened. The capacitive sensors reliably detected eye movement in both conditions. The amplitudes were larger when the eyelids opened. The ability of the sensors to detect eye movement with the closed eyelids would allow the sensors to be used in sleep studies.

Figure 9G:
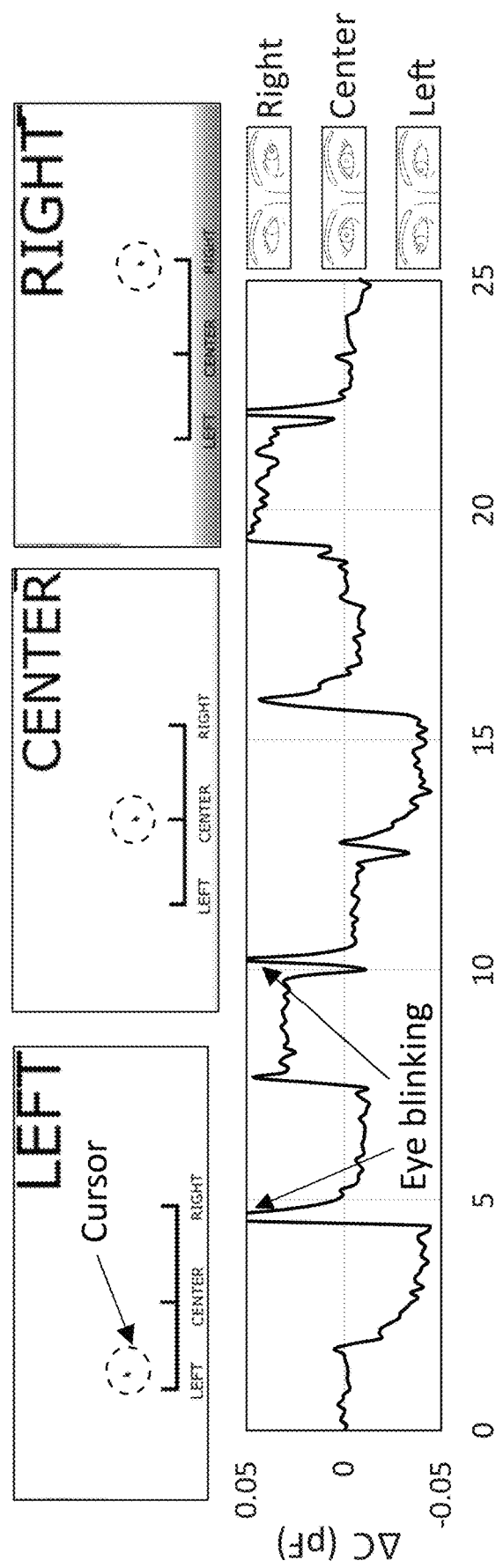
FIG. 9G is a demonstration of a real-time response for detecting eye movement, in accordance with the present technology.

FIG. 9G is a demonstration of a real-time response for detecting eye movement, in accordance with the present technology. To demonstrate the real-time response for detecting eye movement, the capacitive sensing eye tracker was interfaced with a laptop computer to control a cursor on the screen. Starting from a center point, the eyes moved to the left, center, and right locations according to verbal signals. The cursor showed corresponding movements to the three locations. Eye blinking (arrows) did not appear to affect the accuracy of the cursor placements as shown in the supporting video clip (Supporting Information, Real eye tracking HMI.mp4). The wearable eye tracker demonstrated the capability to control a machine using eyeball movement. Eyes are controlled at the left, center, and right locations.

For a capacitive eye tracker, the performance of a high accuracy capacitance-to-digital chip was crucial for accurate detection of eye movement. In our tests, various chips were tested, including AD7747 (Analog Devices), FDC1004 (Texas instrument), and FDC2214 (Texas instrument). Also, a LM 555 timer (Texas instrument) could be used for capacitive eye tracking. According to our characterization, 0.1 fF of accuracy was critical to obtain 1 degree of accuracy for eye movement. In this regard, AD7747 was the best in terms of accuracy. Despite of the lower accuracy of FDC 1004 (1 fF), the higher sampling rate upto 400 Hz could be useful for ultimate eye tracking. FDC 2214 was an electrical resonance circuit with operation frequency of 1~3 MHz. Due to the resonance, the ΔC was high with the increased noise level. The sampling rate of FDC 2214 could be increased to 1 kHz, which had a potential for eye tracking.

TABLE 1

Comparison of the capacitive eye tracker to a commerical eye tracker based on a camera system

| | CPC Eye Tracker | Tobii Pro Glasses 3 | Tobii Pro Nano |
|---|---|---|---|
| Eye Tracking Technique | Capacitive | Corneal reflection | Corneal reflection |
| Binocular Eye Tracking | Capable | Yes | Yes |
| Wearable | Yes | Yes | No (desktop) |
| Sampling Rate | 45 Hz | 50 or 100 Hz | 60 Hz |
| Resolution | 1.1° - Vertical 0.8° - Horizontal | 0.6° | 0.3° |
| Eye tracking for closed eyes | Yes | No | No |
| Wireless communication | Radio Frequency | No | No |
| Scene camera | No | Yes | No |
| Weight (eyeglasses frame + recording unit + battery) | 40 g | 389 g | 59 g |
| Input Voltage | 5 VDC | 5.5 VDC | 5 VDC |
| Battery energy capacity | 100 mAh | 3400 mAh | N/A |

In comparison to a camera based eye tracker (Tobii Nano Pro), the presented capacitive eye tracker demonstrated better features for wearable eye tracking. A more Pragmatic comparison could be made against a wearable eye tracker (Tobii Pro Glasses 3).

Table 1 provides a comparison of the capacitive eye tracker to the other commercial eye trackers. Overall, the capacitive eye tracker has advantage for a wearable eye tracker depending on the weight, computational cost, and production cost. To improve the accuracy of the capacitive eye tracker, a capacitance-to-digital chip that can handle eight sensors with high accuracy and high sampling rate needs to be customized for binocular eye tracking. Also the usability of a capacitive eye tracker needs to be improved to unhinder eye sight and easy calibration.

The capacitive eye tracker was demonstrated to monitor eye movement. Based on our numerical analysis, a hybrid capacitive sensor made of fibrous and rectangular electrodes had the highest sensitivity because of the reduced initial capacitance and increased capacitance change in the presence of an eyeball. In comparison to a single sensor, a differential sensor configuration showed the better detection performance. In the study using a face model, the human charge increased capacitance change ($\Delta C$), but the face background reduced $\Delta C$ of eye movement. In the human subject test, the single capacitive measurement was optimal for vertical eye movement at the locations of (0, 20)~(0, 10) mm relative to the center of the cornea. For horizontal eye movement, the differential capacitive methods allowed accurate measurement at the locations between [(−20, 0) & (20, 0)] and [(−20, 0) & (30, 0)]. The accuracies for vertical and horizontal movement were 1.1 and 0.82 degrees, respectively. The comparison of a capacitive eye tracker to a commercial eye tracker showed a good correlation for horizontal- and vertical eye movements. The horizontal capacitive sensor showed similar $\Delta C$ magnitude to both vertical and horizontal movements, meaning that the magnitude of the vertical eye movement needed to be used to estimate vertical or horizontal movement. A phase diagram between vertical and horizontal signals was used to qualitatively assess eye movement. The presented capacitive eye tracker detected horizontal eye movement with the closed and open eyelids. The relationship between cornea and eyelid position was studied to understand their consequence on the capacitance signal. The cornea was found to dominate the capacitance signal, until the eyelid was fully closed. A real-time control of a laptop cursor was demonstrated based on a subject's horizontal eye movement. The presented wearable capacitive eye tracker shows potential for eye tracking in various fields, including neuroscience, cognitive science, eye function diagnosis, and entertainment.

While illustrative embodiments have been illustrated and described, it will be appreciated that various changes can be made therein without departing from the spirit and scope of the invention.

The embodiments of the invention in which an exclusive property or privilege is claimed are defined as follows:

1. An eye-tracking system, comprising:
   at least one vertical capacitance sensor, configured to measure the vertical position of a cornea of a user's eye by sensing a position of an eyeball and an eyelid of the user; and
   at least one horizontal capacitance sensor, configured to measure the horizontal position of the cornea of the user's eye by sensing a position of the user's eyeball,
   wherein the horizontal and vertical sensors are rotated up to 45 degrees clockwise to increase sensitivity to eye movement.

2. The eye-tracking system of claim 1, further comprising a second horizontal capacitance sensor.

3. The eye-tracking system of claim 2, wherein the at least one horizontal capacitance sensor and the second horizontal capacitance sensor operate using differential measurement to measure the horizontal position of the cornea of the user's eye.

4. The eye-tracking system of claim 1, further comprising a second vertical capacitance sensor.

5. The eye-tracking system of claim 4, wherein the at least one vertical capacitance sensor and the second vertical capacitance sensor operate using differential measurement to measure the vertical position of the cornea of the user's eye.

6. The eye-tracking system of claim 1, wherein the at least one vertical capacitance sensor is configured to be within 30 mm of the user's eyelid covering the cornea and the vertical sensor is positioned within +/−45 mm from a center of the cornea.

7. The eye-tracking system of claim 1, wherein the at least one horizontal sensor is positioned within the range of −30 mm towards a nose of the user to 40 mm away as measured from the center of the cornea.

8. The eye-tracking system of claim 1, wherein the total number of horizontal sensors is 2 or fewer.

9. The eye-tracking system of claim 1, wherein the total number of vertical sensors is 2 or fewer.

10. The eye-tracking system of claim 1, wherein the at least one vertical sensor and the at least one horizontal sensor are mounted on an article configured to be positioned close to the user's eye.

11. The eye-tracking system of claim 10, wherein the article is selected from monocular or binocular lenses, eyeglass frames, an eye mask, goggles, and a mechanical support or adjustable ring configured to suspend the sensors in space above the eye.

12. The eye-tracking system of claim 1, wherein the at least one vertical capacitance sensor is comprised of a single electrode.

13. The eye-tracking system of claim 1, wherein the at least one vertical capacitance sensor is comprised of a first vertical electrode, and a second vertical electrode.

14. The eye tracking system of claim 13, wherein the first vertical electrode is a carbon-nanotube paper composite electrode, and the second vertical electrode is a metal electrode.

15. The eye tracking system of claim 13, wherein the first vertical electrode is a first carbon nanotube paper composite electrode, and the second vertical electrode is a second carbon nanotube paper composite electrode.

16. The eye tracking system of claim 13, wherein the first vertical electrode and the second vertical electrode are coated with an electrically conductive ink.

17. The eye tracking system of any of claim 13, wherein there is a gap between the first vertical electrode and the second vertical electrode.

18. The eye tracking system of claim 17, wherein the gap between the first vertical electrode and the second vertical electrode ranges from 300 μm to 1 mm.

19. The eye tracking system of claim 1, wherein the at least one horizontal capacitance sensor is comprised of a single electrode.

20. The eye-tracking system of claim 1, wherein the at least one horizontal capacitance sensor is comprised of a first horizontal electrode, and a second horizontal electrode.

21. The eye tracking system of claim 20, wherein the first horizontal electrode is a carbon-nanotube paper composite electrode, and the second horizontal electrode is a metal electrode.

22. The eye tracking system of claim 20, wherein the first horizontal electrode is a first carbon nanotube paper composite electrode, and the second horizontal electrode is a second carbon nanotube paper composite electrode.

23. The eye tracking system of claim 20, wherein the first horizontal electrode and the second horizontal electrode are coated with an electrically conductive ink.

24. The eye tracking system of claim 20, wherein there is a gap between the first horizontal electrode and the second horizontal electrode.

25. The eye tracking system of claim 24, wherein the gap between the first horizontal electrode and the second horizontal electrode ranges from 300 μm to 5 mm.

26. The eye-tracking system of claim 1, further comprising an electronic control unit configured to control, and receive measurement signals from, the at least one horizontal sensor and the at least one vertical sensor.

27. The eye-tracking system of claim 26 further comprising instructions executable on the processor configured to apply machine learning and/or artificial intelligence to provide the output indicative of the position of the user's eye.

28. A method of tracking a position of at least one eye of a user, comprising: mounting an eye-tracking system according to claim 1 to the user; and measuring capacitance from the at least one vertical sensor and the at least one horizontal sensor.

29. An eye-tracking system comprised of:
an article comprising a left side and a right side;
a first vertical sensor attached to the right side of the article;
a second vertical sensor attached to the left side of the article;
a first horizontal sensor attached to the right side of the article; and
a second horizontal sensor attached to the left side of the article;
wherein the first vertical sensor and the first horizontal sensor are configured to measure a vertical position and a horizontal position, respectively, of a cornea of a user's right eye by sensing a position of a right eyelid of the user and the user's right eyeball,
wherein the horizontal and vertical sensors are rotated up to 45 degrees clockwise to increase sensitivity to eye movement, and
wherein the second vertical sensor and the second horizontal sensor are configured to measure a vertical position and a horizontal position, respectively, of a cornea of a user's left eye by sensing a position of a left eyelid of the user and the user's left eyeball, so that both a user's right eye movements and left eye movements are sensed simultaneously.

* * * * *